US008313906B2

(12) United States Patent
Cao et al.

(10) Patent No.: US 8,313,906 B2
(45) Date of Patent: Nov. 20, 2012

(54) METHODS AND SYSTEMS FOR MICROFLUIDIC DNA SAMPLE PREPARATION

(75) Inventors: Weidong Cao, Rockville, MD (US); Hiroshi Inoue, Bethesda, MD (US); Kevin Louder, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 310 days.

(21) Appl. No.: 12/505,202

(22) Filed: Jul. 17, 2009

(65) Prior Publication Data

US 2010/0021910 A1    Jan. 28, 2010

Related U.S. Application Data

(60) Provisional application No. 61/081,967, filed on Jul. 18, 2008.

(51) Int. Cl.
 C12Q 1/68 (2006.01)
 C12M 1/00 (2006.01)
 C07H 21/00 (2006.01)
(52) U.S. Cl. .......... 435/6.1; 435/283.1; 536/22.1; 536/25.4
(58) Field of Classification Search .......... 435/6.1, 435/91.2, 283.1; 536/22.1, 25.4
 See application file for complete search history.

(56) References Cited

U.S. PATENT DOCUMENTS

| | | | |
|---|---|---|---|
| 4,752,564 A | 6/1988 | Hopkins | |
| 5,118,428 A | 6/1992 | Sand et al. | |
| 5,447,864 A | 9/1995 | Raybuck et al. | |
| 5,482,829 A | 1/1996 | Kass et al. | |
| 5,501,954 A * | 3/1996 | Mahr et al. | 435/6.16 |
| 5,643,455 A | 7/1997 | Kopp et al. | |
| 5,736,033 A | 4/1998 | Coleman et al. | |
| 5,789,243 A * | 8/1998 | Boquet | 435/306.1 |
| 6,074,827 A * | 6/2000 | Nelson et al. | 435/6.12 |
| 6,306,590 B1 * | 10/2001 | Mehta et al. | 435/6.19 |
| 6,322,983 B1 | 11/2001 | Burgoyne | |
| 6,352,838 B1 | 3/2002 | Krulevitch et al. | |
| 6,387,290 B1 | 5/2002 | Brody et al. | |
| 6,605,454 B2 * | 8/2003 | Barenburg et al. | 435/173.7 |
| 6,811,695 B2 * | 11/2004 | Karp | 210/321.6 |
| 6,827,095 B2 | 12/2004 | O'Connor et al. | |
| 6,852,851 B1 | 2/2005 | Tooke et al. | |
| 6,878,271 B2 | 4/2005 | Gilbert et al. | |
| 6,914,137 B2 | 7/2005 | Baker | |
| 6,919,046 B2 | 7/2005 | O'Connor et al. | |
| 6,960,437 B2 * | 11/2005 | Enzelberger et al. | 435/6.19 |
| 6,992,181 B2 | 1/2006 | Tooke et al. | |
| 7,078,191 B1 * | 7/2006 | Wanker et al. | 435/69.7 |
| 7,160,423 B2 | 1/2007 | Chien et al. | |
| 7,192,557 B2 | 3/2007 | Wu et al. | |
| 7,258,976 B2 * | 8/2007 | Mitsuhashi | 435/6.1 |
| 7,262,283 B2 | 8/2007 | Hendriks et al. | |
| 7,279,134 B2 * | 10/2007 | Chan et al. | 422/503 |
| 7,294,503 B2 | 11/2007 | Quake et al. | |
| 7,320,862 B2 * | 1/2008 | Stahler et al. | 435/6.11 |
| 2002/0055184 A1 * | 5/2002 | Naylor et al. | 436/514 |
| 2005/0042639 A1 | 2/2005 | Knapp et al. | |
| 2005/0142570 A1 | 6/2005 | Parthasarathy et al. | |
| 2005/0142663 A1 | 6/2005 | Parthasarathy et al. | |
| 2006/0024712 A1 | 2/2006 | Baker et al. | |
| 2006/0134599 A1 | 6/2006 | Toner et al. | |
| 2007/0026381 A1 | 2/2007 | Huang et al. | |
| 2007/0031289 A1 * | 2/2007 | Cox et al. | 422/73 |
| 2007/0037966 A1 * | 2/2007 | Rasmussen et al. | 530/383 |
| 2007/0068812 A1 | 3/2007 | Han et al. | |
| 2007/0072229 A1 * | 3/2007 | Bialozynski et al. | 435/6 |
| 2008/0003588 A1 | 1/2008 | Hasson et al. | |
| 2008/0003593 A1 | 1/2008 | Hasson et al. | |
| 2008/0130971 A1 | 6/2008 | Hasson et al. | |
| 2008/0131955 A1 | 6/2008 | Stone | |
| 2008/0176230 A1 | 7/2008 | Owen et al. | |
| 2009/0053726 A1 | 2/2009 | Owen et al. | |
| 2009/0101559 A1 * | 4/2009 | Bala Subramaniam et al. | 210/194 |
| 2009/0111149 A1 | 4/2009 | Cao | |
| 2009/0165876 A1 * | 7/2009 | Atkin et al. | 137/825 |
| 2009/0176899 A1 * | 7/2009 | Yoo et al. | 521/50.5 |
| 2010/0021910 A1 * | 1/2010 | Cao et al. | 435/6 |
| 2011/0014605 A1 * | 1/2011 | Stone | 435/6 |

FOREIGN PATENT DOCUMENTS

| | | |
|---|---|---|
| GB | 2355717 A | 5/2001 |
| WO | 88/05331 | 7/1988 |
| WO | 2006/004611 A2 | 1/2006 |

OTHER PUBLICATIONS

Vindelov et al., A detergent-trypsin method for the preparation of nuclei for flow cytometric DNA analysis. Cytometry 3 (5) : 323 (1983).*
Watson N., Isolation and use of mammalian cell nuclei. Life Science Quarterly (Jul. 2000).*
Boom et al., J. Clin. Microbiol., 28(3):495-503 (1990) (abstract).
Bøyum, Nature, 204:793-794 (1964) (abstract).
Breadmore et al., Anal. Chem. 75(8):1880-1886 (2003) (abstract).
Chen et al., Anal. Biochem., 101(2):339-341(1980) (abstract).
Chen et al., Sensors and Actuators B: Chemical, 130(1):216-221 (2008) (abstract).
Cheng et al., Nucleic Acids Research, 24(2):380-385 (1996).
Dignam et al., Nucleic Acids Res., 11(5):1475-1489 (1983).
Li et al., Eukaryotic Cell, 2(5):1091-1098 (2003) (abstract).
Marko et al., Anal. Biochem., 121(2):382-387 (1982) (abstract).
Melzak et al., J. Colloid and Interface Science, 181(2):635-644 (1996) (abstract).
Service, Science, 282(5388):399-401 (1998) (abstract).

(Continued)

*Primary Examiner* — Ethan C Whisenant
(74) *Attorney, Agent, or Firm* — Rothwell, Figg, Ernst & Manbeck, P.C.

(57) ABSTRACT

The present invention relates to methods and systems for microfluidic DNA sample preparation. More specifically, embodiments of the present invention relate to methods and systems for the isolation of DNA from patient samples on a microfluidic device and use of the DNA for downstream processing, such as performing amplification reactions and thermal melt analysis on the microfluidic device.

52 Claims, 24 Drawing Sheets

OTHER PUBLICATIONS

Sethu et al., Anal. Chem., 76(21):6247-6253 (2004) (abstract).
Sethu et al., Anal. Chem., 78(15):5453-5461 (2006) (abstract).
Vandelinder et al., Anal. Chem., 78(11):3765-3771 (2006) (abstract).
Vandelinder et al., Anal. Chem., 79(5):2023-2030 (2007) (abstract).

* cited by examiner

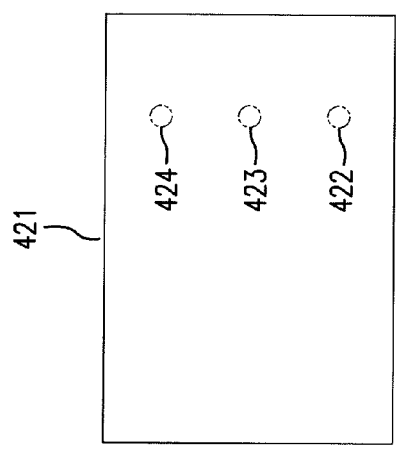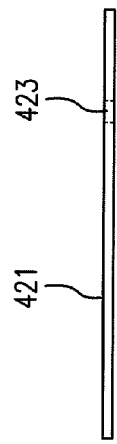

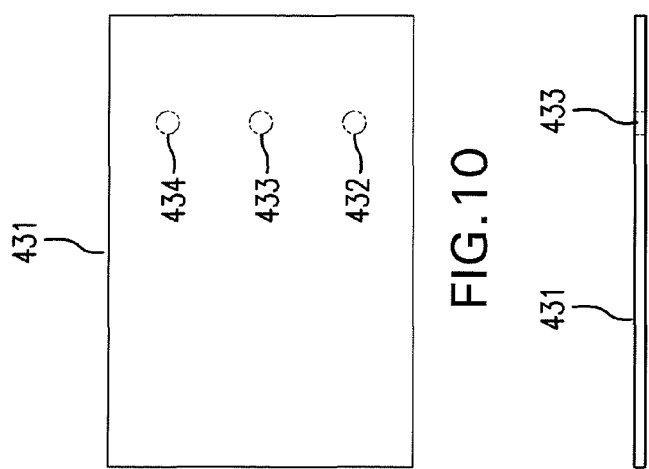
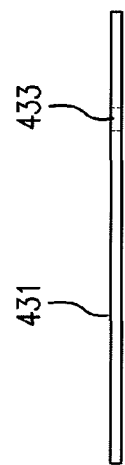
FIG.10
FIG.11

METHODS AND SYSTEMS FOR MICROFLUIDIC DNA SAMPLE PREPARATION

CROSS-REFERENCE TO RELATED APPLICATIONS

This application claims the benefit of U.S. Provisional Patent Application Ser. No. 61/081,967, filed on Jul. 18, 2008, which is incorporated herein by reference in its entirety. This application is related to U.S. patent application Ser. No. 12/505,195, filed on Jul. 17, 2009, entitled "METHODS AND SYSTEMS FOR DNA ISOLATION ON A MICROFLUIDIC DEVICE," and naming Michele R. Stone as the inventor, which application is incorporated herein by reference in its entirety.

BACKGROUND

1. Field of the Invention

The present invention relates to methods and systems for microfluidic DNA sample preparation. More specifically, embodiments of the present invention relate to methods and systems for the isolation of DNA from patient samples on a microfluidic device and use of the DNA for downstream processing, such as performing amplification reactions and thermal melt analysis on the microfluidic device.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is perhaps the most well-known of a number of different amplification techniques.

PCR is one of the more sensitive methods for nucleic acid analysis. However, many substances in clinical samples, including blood, can affect PCR and can result in substantial error in the PCR results. Thus, DNA isolation and purification are critical to methods for DNA analysis. Conventional DNA preparation requires large volume samples and requires a long process time. Microfluidic technology makes it possible to use much less sample and less time for DNA sample preparation. Solid phase extraction methods have been applied in DNA sample preparation. DNA is selectively extracted on the solid phase while other substances in the sample are washed out of the extraction column. For instance, Breadmore et al. (*Anal Chem* 75(8): 1880-1886, 2003) reported on a microchip-based DNA purification method using silica beads packed into glass microchips and immobilized within a sol-gel. Alternatively, DNA isolation can be achieved by nuclei size sieving.

Since DNA only exists in the nuclei of cells, DNA samples can be prepared by selectively isolating nuclei from the sample. Traditional nuclei isolation is slow and has low efficiency. Generally, nuclei isolation is performed by selective lysis of cellular membranes while keeping the nuclei intact. Nuclei are then isolated by centrifuge, sediment or sieving. Dignani et al. (*Nucl Acids Res* 11: 1475-1489, 1983) reported isolation of nuclei from samples by centrifugation. U.S. Pat. No. 5,447,864 discloses a method of isolating nuclei using a DNA mesh. U.S. Pat. No. 6,852,851 discloses a method of isolating nuclei in a microfabricated apparatus that contains a plurality of radially dispersed micro-channels. U.S. Pat. No. 6,992,181 describes the use of a CD device for the purification of DNA or cell nuclei. This method requires moving parts and centrifugal force to isolate DNA and or cell nuclei, using a barrier in the channel to impede flow of DNA and nuclei. Palaniappan et al. (*Anal Chem* 76:6247-6253, 2004) reported a continuous flow microfluidic device for rapid erythrocyte lysis. VanDelinder et al. (*Anal Chem* 78:3765-3771, 2006) reported a separation of plasma from whole human blood in a continuous cross-flow in a molded microfluidic device. To increase mixing of lysis buffer with blood sample in microfluidic channel, Palaniappan et al. (*Anal Chem* 78:5453-5461, 2006) reported a microfluidic channel with the channel floors that are patterned with double herringbone microridges. VanDelinder et al. (*Anal Chem* 79:2023-2030, 2007) describe a perfusion in microfluidic cross-flow for particles and cells. Particles flow in the main channel while a perfusion flows through the side channels to exchange the medium of suspension.

There are several problems with current technology of purifying DNA by isolating nuclei from cells. First, the conventional approach is slow. Usually, the conventional approach takes hours to finish from cell lysis to the nuclei isolation. For example, the purification process described in U.S. Pat. No. 6,852,851 is carried out in a plurality of micro channels with a mesh built into the micro channel. However, because the size of micro channels is limited, the process can treat only limited sample sizes from 100 nl to 1 μl. Another problem is with the method of releasing DNA and/or nuclei from membrane. For example, DNAse is used in U.S. Pat. No. 5,447,864 to release nuclei from membrane. However, the addition of DNAse will fail the down stream process. In U.S. Pat. No. 5,447,864, sodium dodecyl sulfate solution or proteinase K is used to disrupt the nuclear envelope in order to release DNA. However, these lysis reagents will also seriously inhibit the downstream process. The conventional nuclear lysis method is to use high concentration sodium chloride (0.5 M) to disrupt the nuclear membrane. However, the high concentration sodium chloride will also inhibit the downstream process.

In addition, the current technologies require specific buffers for DNA binding and washing, most of which are not compatible with down stream applications such as PCR. These technologies also have a wide range of efficiencies in the overall quantity of DNA that is purified. This can be a significant problem when samples are to be used in microfluidics. The multiple reagents that are typically required for DNA purification would demand that moving parts, such as valves, be constructed into a microfluidic device for the introduction of multiple reagents in a solid phase extraction. In a microfluidic system, solid phase extraction or the use of multiple reagents is complicated and can lead to system failures.

Although the various methods exist to capture nuclei for use in down stream application or to separate specific cells from a sample population, none of these methods describes a single device that is capable of extracting cell nuclei and isolating the nucleic acid contained in the cell nucleic that is suitable for microfluidic processing and down stream processes such as amplification reactions and detection analysis. Thus, there is a need to develop microfluidic systems and methods for DNA isolation.

SUMMARY OF THE INVENTION

The present invention relates to methods and systems for microfluidic DNA sample preparation. More specifically, embodiments of the present invention relate to methods and systems for the isolation of DNA from patient samples on a microfluidic device and use of the DNA for downstream processing, such as performing amplification reactions and thermal melt analysis on the microfluidic device.

In one aspect, the present invention provides a method of purifying DNA from a sample (e.g., a patient sample or other sample) in a microfluidic device. According to this aspect, the method comprises: (a) mixing the sample and a lysis buffer in a mixing region of a microfluidic device; (b) selectively lysing the cellular membranes of cells in the sample without lysing the nuclear membranes of cells in a cell lysing region of the microfluidic device to produce intact nuclei from the cells; (c) trapping the intact nuclei from the sample on a membrane in a cell trapping region of the microfluidic device while allowing other components of the sample to flow through the membrane and into a waste collection region of the microfluidic device; (d) lysing the intact nuclei trapped on the membrane; (e) releasing the DNA from the lysed nuclei; and (f) collecting the released DNA in a DNA collection region of the microfluidic device.

In some embodiments, the sample is a patient sample which could be, for example, a blood sample, a urine sample, a saliva sample, a sputum sample, a cerebrospinal fluid sample, a body fluid sample or a tissue sample which contain white blood cells. In other embodiments, the patient sample comprises white blood cells. In additional embodiments, the patient sample is first enriched for white blood cells prior to the selective lysis of the cellular membrane. In some embodiments, the enrichment of white blood cells is performed by filtration. In additional embodiments, the enrichment of white blood cells is performed using antibodies. In some embodiments, the antibodies are coupled to a solid phase, such as beads, magnetic beads, particles, polymeric beads, chromatographic resin, filter paper, a membrane or a hydrogel.

In some embodiments, the selective lysis is performed by contacting the patient sample, either whole or after white blood cell enrichment, with a buffer (referred to herein as a lysis buffer or nuclei isolation buffer) that selectively permeabilizes cellular membranes while leaving the nuclei of the cells intact. Nuclei isolation buffers that have these characteristics are well known to the skilled artisan. Products that include nuclei isolation buffers for selectively lysing cellular membranes are commercially available. Suitable commercial products that include such buffers, include, but are not limited to, Nuclei EZ Prep Nuclei Isolation Kit (NUC-101) (Sigma, St. Louis, Mo., USA), Nuclear/Cytosol Fractionation Kit (K266-100) (BioVision Research Products, Mountain View, Calif., USA), NE-PER Nuclear and Cytoplasmic Extraction Reagents (Pierce, Rockville, Ill., USA), Nuclear Extraction Kit (Imgenex, Corp., San Diego, Calif., USA), Nuclear Extract Kit (Active Motif, Carlsbad, Calif., USA), and Qproteome Nuclear Protein Kit (Qiagen, Valencia, Calif., USA). See also, U.S. Pat. Nos. 5,447,864, 6,852,851 and 7,262,283. It is known that the type of nuclei in question may determine which nuclei isolation buffer will be required. See, U.S. Pat. No. 5,447,864 for a discussion of factors that can be optimized for preparing a suitable selective lysis buffer for different cell types.

In one embodiment, the lysis buffer is a hypotonic buffer. For example, a commercial hypotonic lysis buffer can be purchased from Sigma Aldrich, Nuclei EZ lysis buffer (N 3408). A kit is also available from Sigma Aldrich, Nuclei EZ Prep Nuclei Isolation Kit (Nuc-101). A common recipe for a 10× hypotonic solution is, 100 mM HEPES, pH 7.9, with 15 mM $MgCl_2$ and 100 mM KCl. In another embodiment, the lysis buffer is a hypotonic buffer that comprises a detergent. Suitable detergents include, but are not limited to ionic detergents, such as lithium lauryl sulfate, sodium deoxycholate, and Chaps, or non-ionic detergents, such as Triton X-100, Tween 20, Np-40, and IGEPAL CA-630. In another embodiment, the lysis buffer is an isotonic buffer. For example, Sigma Aldrich offers a kit, CelLytic Nuclear Extraction kit, which contains an isotonic lysis buffer. A common recipe for a 5× isotonic lysis buffer is, 50 mM Tris HCl, pH 7.5, with 10 mM $MgCl_2$, 15 mM $CaCl_2$, and 1.5M Sucrose. In an additional embodiment, the buffer is an isotonic buffer that comprises a detergent which may be an ionic detergent or a non-ionic detergent. In other embodiments, the selective lysis is performed using a hypotonic lysis buffer that contains a weak detergent. In further embodiments, the patient sample and the hypotonic lysis buffer are mixed in a 1:1 ratio. In additional embodiments, the selective lysis of the cellular membranes totally lyses red blood cells.

In some embodiments, the steps of lysing the intact nuclei trapped on the membrane and releasing the DNA from the lysed nuclei comprise flowing an elution buffer over the intact nuclei trapped on the membrane.

In some embodiments, the elution buffer is a buffer in which the DNA is compatible. In other embodiments, elution buffer comprises a Tris buffer, KCl and a zwitterion. In one embodiment, the zwitterion is betaine, trimethylamine-N-oxide, trimethylamine hydrochloride or trimethylamine bromide. In other embodiments, the elution buffer is an amplification reaction buffer that may contain the non-assay specific amplification reagents. In additional embodiments, the amplification reaction buffer is a PCR buffer that may contain the non-assay specific PCR reagents. In further embodiments, the elution buffer contains a dye that binds to DNA. In additional embodiments, the dye is useful for quantifying the amount of DNA in the channel. In additional embodiments, the nuclei are lysed by heat to release the DNA from the nuclei. In some embodiments, the nuclei are subjected to heat prior to an amplification reaction. In other embodiments, the nuclei are subjected to heat during the amplification reaction and the nuclei lysis region is the initial region of microfluidic device in which the amplification reaction is conducted.

In some embodiments, the intact nuclei trapped on the membrane are lysed by applying heat to the trapped nuclei. In one embodiment, the trapped nuclei are heated for approximately 1 to 10 minutes at a temperature in the range of approximately 35° C. to 95° C. In another embodiment, the trapped nuclei are heated for approximately 7 minutes at a temperature of approximately 50° C. In a further embodiment, the DNA released from the lysed nuclei flows to the DNA collection region of the microfluidic device by flowing an elution buffer over the DNA. In some embodiments, the elution buffer is as described herein.

In another aspect, the present invention provides a microfluidic device for purifying DNA from a patient sample. In accordance with this aspect, the microfluidic device comprises a sample port and lysis buffer port in fluid communication with a mixing region of the microfluidic device. The mixing region is configured to permit mixing of a patient sample from the sample port and lysis buffer from the lysis buffer port. The microfluidic device also comprises a cell lysis region in fluid communication with the mixing region. The cell lysis region is configured to permit the lysis buffer to selectively lyse cellular membranes of cells in the patient sample without lysing nuclear membranes of the cells to produce intact nuclei from the cells in the patient sample. The microfluidic device further comprises a nuclei trapping region wherein intact nuclei from the patient sample are trapped on a membrane while other components of the patient sample flow through the membrane and into a waste collection region of the microfluidic device. The nuclei trapping region is in fluid communication with the cell lysis region. The microfluidic device also comprises a nuclei lysis region in which the nuclear membranes of the intact nuclei are lysed to release the DNA. The microfluidic device further comprises a DNA collection region in the microfluidic device wherein DNA released from the trapped intact nuclei is collected.

In some embodiments, the microfluidic device further comprises an elution buffer port in fluid communication with the nuclei trapping region and the nuclei lysing region. The elution buffer from the elution buffer port can be controlled to flow through the nuclei trapping region and the nuclei lysing region to lyse the nuclear membranes of the trapped intact nuclei to release the DNA. In one embodiment, the elution buffer is one in which the DNA is compatible. In other embodiments, elution buffer comprises a Tris buffer, KCl and a zwitterion. In one embodiment, the zwitterion is betaine, trimethylamine-N-oxide, trimethylamine hydrochloride or trimethylamine bromide. In other embodiments, the elution buffer is an amplification reaction buffer that may contain the non-assay specific amplification reagents. In additional embodiments, the amplification reaction buffer is a PCR buffer that may contain the non-assay specific PCR reagents.

In some embodiments, the microfluidic device further comprises a heat source which is configured to provide heat to the intact nuclei in the nuclei lysis region sufficient to lyse the nuclear membranes thereby releasing the DNA. In one embodiment, the heat source is controlled to heat the nuclei for approximately 1 to 10 minutes at a temperature in the range of approximately 35° C. to 95° C. In another embodiment, the heat source is controlled to heat the nuclei for approximately 7 minutes at a temperature of approximately 50° C.

In some embodiments, the DNA released from the lysed nuclei flows to the DNA collection region of the microfluidic device by flowing an elution buffer over the DNA. In other embodiments, the membrane is made of silicon, glass, polymers, polyester, polycarbonate or nitrocellulose. In additional embodiments, the membrane has a round or rectangular shape. In one embodiment, the membrane has a pore size from approximately 500 nm to 10 µm. In another embodiment, the membrane has a pore size from approximately 0.5 µm to 10 µm.

In some embodiments, the microfluidic device comprises multiple layers. In one embodiment, the microfluidic device further comprises: (1) a first layer comprising the lysis buffer port, the patient sample port, an elution buffer port, a purified DNA collection port and a waste port; (2) a second layer comprising a network of microchannels that transports the lysis buffer solution and the patient sample to the mixing region of the microfluidic device; (3) a third layer comprising a network of microchannels; (4) the membrane located between the second and third layers. In some embodiments, the patient sample and the lysis buffer solution mix in the mixing region and flow in the microchannels to the cell lysis region, and wherein the patient sample and the lysis buffer solution flow from the cell lysis region to the membrane in the nuclei trapping region, and wherein the other components of the patient sample flow through the membrane and into a microchannel in the third layer and to the waste collection region of the microfluidic device, and wherein the DNA released from the nuclei flows through the membrane and into a microchannel located in the third layer and to the DNA collection region.

In other embodiments, the microfluidic device further comprises: (1) a first layer comprising the lysis buffer port, the patient sample port, an elution buffer port, a purified DNA collection port and a waste port; (2) a second layer comprising a network of microchannels that transports the lysis buffer solution and the patient sample to the mixing region of the microfluidic device; (3) a third layer comprising a hole through which fluid flows from the microchannels in the second layer and onto the membrane; (4) a fourth layer comprising a hole through which fluid flows from the membrane and into microchannels located in a fifth layer, therein the fifth layer further comprising the waste collection region and the DNA collection region.

In another aspect, the present invention provides another microfluidic device for purifying DNA from a patient sample. In accordance with this aspect, the microfluidic device comprises a cell lysis region configured such that a lysis buffer is permitted to mix with the patient sample resulting in the selective lysing of cellular membranes of cells in the patient sample without lysing nuclear membranes of the cells to produce intact nuclei from the cells in the patient sample. The microfluidic device also comprises a cross-flow filtration region in which intact nuclei are separated from other components of the patient sample by a filter. The filter has a pore size such that the intact nuclei do not pass through the filter and the other components of the patient sample pass through the filter and are carried away by a cross-flow buffer that is controlled to flow through the cross-flow filtration region. The microfluidic device further comprises an interface channel in fluid communication with said cross-flow filtration region through which purified nuclei flow for downstream analysis.

In some embodiments, the cross-flow filtration region comprises a microfluidic separation channel in fluid communication with the cell lysis region and configured to receive the intact nuclei and the other components of the patient sample from the cell lysis region. The filter is constructed in the microfluidic channel. The cross-flow filtration region also comprises a cross-flow buffer port configured to permit the cross-flow buffer to flow across the microfluidic separation channel and through the filter. The cross-flow buffer, as it flows across the separation channel, facilitates removal of the other contents of the patient sample from the separation channel through the filter. The intact nuclei flow through the separation channel.

In some embodiments, the flow of one of the lysed patient sample and the cross-flow buffer is driven by a pressure differential and the flow of the other of the lysed patient sample and cross-flow buffer is driven by an electrophoretic voltage potential. In one embodiment, the pore size of the filter is between approximately 2 µm to 10 µm. In another embodiment, the pore size of the filter is approximately 5 µm. In one embodiment, the filter is a membrane. In another embodiment, the filter is an array of pillars that forms as size exclusion barrier.

In some embodiments, the cross-flow filtration region is configured to separate the intact nuclei, bacteria and viruses from the lysed patient sample. In one embodiment, the cross-flow filtration region comprises a first filter to separate the intact nuclei, a second filter to separate bacteria and a third filter to separate viruses. In another embodiment, the first filter is located closest to a cross-flow buffer port, the second filter located next closest to the cross-flow buffer port, and the third filter located furthest from the cross-flow buffer port. In a one embodiment, the pore size of the first filter is between approximately 2 µm to 10 µm, the pore size of the second filter is between approximately 0.2 µm to 2 µm, and the pore size of the third filter is between approximately 10 nm to 400 nm. In another embodiment, wherein the pore size of the first filter is approximately 8 µm, the pore size of the second filter is approximately 0.4 µm, and the pore size of the third filter is approximately 100 nm.

In some embodiments, the microfluidic device further comprises more than one cross-flow filtration region in which each cross-flow filtration region receives a portion of the lysed patient sample from the cell lysis region, and each cross-flow filtration region is in fluid communication with one or more interface channels. In one embodiment, the filter of one cross-flow filtration system has a pore size that is different from the pore size of one other cross-flow filtration system.

In some embodiments the microfluidic device further comprises a nuclei concentration region in which the intact nuclei from the cross-flow filtration region are concentrated. In one embodiment, the nuclei concentration region comprises a concentration channel having a sample input section, a sample outlet section and a wall portion configured to prevent intact nuclei from flowing through said wall portion and to allow the other contents of the patient sample to flow through said wall portion. In one embodiment, the wall portion is a filter. In another embodiment, the filter comprises a set of pillars placed along the concentration channel.

In some embodiments, the patient sample is as described herein. In other embodiments, the patient sample comprises white blood cells. In further embodiments, the downstream analysis comprises an amplification reaction in which nucleic acid is amplified and/or a detection procedure for determining the presence or absence of an amplified product.

In another aspect, the present invention provides a microfluidic system for purifying DNA from a patient sample. In accordance with this aspect, the microfluidic system comprises a microfluidic device. The system also comprises a cell lysis region in the microfluidic device configured such that a lysis buffer is permitted to mix with the patient sample resulting in the selective lysing of cellular membranes of cells in the patient sample without lysing nuclear membranes of the cells to produce intact nuclei from the cells in the patient sample. The system further comprises a cross-flow filtration region in the microfluidic device in which intact nuclei are separated from other components of the patient sample by a filter. The filter has a pore size such that the intact nuclei do not pass through the filter and the other components of the patient sample pass through the filter and are carried away by a cross-flow buffer that is controlled to flow through the cross-flow filtration region. The system also comprises a nuclei lysis region in the microfluidic device in which the nuclear membranes of the intact nuclei are lysed to release the DNA. The nuclei lysis region is in fluid communication with the cross-flow filtration region. The system also comprises an amplification reaction region in the microfluidic device in which the nucleic acid is amplified and a detection region in the microfluidic device for determining the presence or absence of an amplified product.

In some embodiments, the nuclei lysis region is part of the amplification reaction region. In other embodiments, the regions are in separate microfluidic devices. In one embodiment, the cell lysis region, the cross-flow filtration region, and the nuclei lysis region are in one microfluidic device and the amplification region and the detection region are in a second microfluidic device.

In another aspect, the present invention provides a method for purifying DNA from a patient sample in a microfluidic device. In accordance with this aspect, the method comprises mixing a patient sample containing cells and a lysis buffer in a mixing region of said microfluidic device. The lysis buffer selectively lyses cellular membranes without lysing nuclear membranes. The method also comprises selectively lysing in a cell lysing region of the microfluidic device the cellular membranes of the cells in the patient sample without lysing the nuclear membranes of the cells to produce intact nuclei from the cells. The method further comprises separating the intact nuclei from the patient sample in a cross-flow filtration region of said microfluidic device. The cross-flow filtration region comprises a filter having a pore size such that the intact nuclei do not pass through the filter and the other components of the patient sample pass through the filter and are carried away by a cross-flow buffer that is controlled to flow through the cross-flow filtration region. The method also comprises flowing purified nuclei through an interface channel in fluid communication with said cross-flow filtration region for downstream analysis.

In some embodiments, the method further comprises driving the flow of one of the lysed patient sample and the cross-flow buffer by a pressure differential and driving the flow of the other of the lysed patient sample and the cross-flow buffer by an electrophoretic voltage potential. In other embodiments, the method further comprises separating the intact nuclei, bacteria and viruses from the lysed patient sample in said cross-flow filtration region in which each of the intact nuclei, bacteria and viruses are released into separate channels with the cross-flow buffer. In another embodiment, the method further comprises separating the intact nuclei, bacteria and viruses from the lysed patient sample in said cross-flow filtration region by a series of filters each having a different pore size. In another embodiment, the method further comprises concentrating the intact nuclei prior to sending the intact nuclei for downstream analysis. In some embodiments, the method further comprises separating the intact nuclei from the lysed patient sample utilizing more than one cross-flow filtration region, each receiving a portion of the lysed patient sample. In some embodiments the patient sample is as described herein. In other embodiments, purifying DNA from cells in a patient sample comprises purifying DNA from white blood cells in the patient sample.

In another aspect, the present invention provides a method of determining the presence or absence of a nucleic acid in a patient sample. In accordance with this aspect, the method comprises mixing a patient sample containing cells and a lysis buffer in a mixing region of said microfluidic device. The lysis buffer selectively lyses cellular membranes without lysing nuclear membranes. The method also comprises selectively lysing in a cell lysing region of the microfluidic device the cellular membranes of the cells in the patient sample without lysing the nuclear membranes of the cells to produce intact nuclei from the cells. The method further comprises separating the intact nuclei from the patient sample in a cross-flow filtration region of the microfluidic device. The cross-flow filtration region comprises a filter having a pore size such that the intact nuclei do not pass through the filter and the other components of the patient sample pass through the filter and are carried away by a cross-flow buffer that is controlled to flow through the cross-flow filtration region. The method also comprises lysing the nuclei to release the nucleic acid in the microfluidic device. The method further comprises amplifying the nucleic acid in the microfluidic device; and determining the presence or absence of an amplified product. The presence of the amplified product indicates the presence of the nucleic acid in the patient sample.

In some embodiments, the patient sample is as described herein. In other embodiments the patient sample contains white blood cells. In additional embodiments, the method further comprises enriching the patient sample for white blood cells prior to the selective lysis of the cellular membranes. The enrichment for white blood cells can be performed as described herein. In further embodiments, the mixing of the patient sample and lysis buffer, selectively lysing, separating intact nuclei and lysing the nuclei are performed in one microfluidic device and the amplification and detection are performed in a second microfluidic device. In other embodiments, the mixing of the patient sample and lysis buffer, selectively lysing and separating intact nuclei are performed in one microfluidic device and the lysing the nuclei, amplification and detection are performed in a second microfluidic device.

In another aspect, the present invention provides another microfluidic system for isolating DNA from cells in a patient sample. In accordance with this aspect, the microfluidic system comprises a lysis buffer storage device for storing a lysis buffer in which the lysis buffer selectively lyses cellular membranes without lysing nuclear membranes. The system also comprises an elution buffer storage device for storing an elution buffer. The system further comprises a sample card having multiple chambers for receiving the patient sample. Each chamber in the sample card comprises an inlet, a filter and an outlet. The system also comprises a flow control system for controlling flow of the lysis buffer and the elution buffer to each chamber of the sample card. The flow control system controls the flow of lysis buffer into each chamber of the sample card such that the lysis buffer selectively lyses cellular membranes to release nuclei and cell debris causing the cell debris to flow through the filter into a waste receptacle positionable beneath the sample card and without lysing nuclear membranes of nuclei in the patient sample which become trapped on the filter. The system further comprises a temperature control system for heating the filter in the sample card sufficient to lyse nuclei trapped on said filter and release DNA. The system also comprises an interface chip comprising multiple DNA sample wells and DNA sample outlets. The interface chip is positionable beneath the sample card and is configured to receive the DNA released from the lysed nuclei trapped on said filter. The system further comprises a main controller in communication with the temperature control system, and the flow control system.

In some embodiments, the temperature control system comprises a heating source and a heat sensor. In other embodiments, the flow control system comprises a pump and a solution delivery chip, wherein the solution delivery chip comprises multiple channels for delivering lysis buffer and elution buffer to each chamber of the sample card. In further embodiments, the flow control system further comprises a pressure control system. The pressure control system comprises an air source, a pressure sensor for controlling the delivery of the elution buffer and the lysis buffer to each chamber of the sample card. In some embodiments, the multiple chambers of the sample card are in fluid communication with one another. In other embodiments, the sample card is disposable. In some embodiments, the sample card is configured to contain multiple different patient samples. In other embodiments, the sample card is configured to contain one patient sample in multiple chambers.

In another aspect, the present invention provides a microfluidic system for determining the presence or absence of a nucleic acid in a patient sample. In accordance with this aspect, the microfluidic system comprises a microfluidic device comprising a sample preparation region, an amplification reaction region and a detection region. The sample preparation region comprises a lysis buffer storage device for storing a lysis buffer in which the lysis buffer selectively lyses cellular membranes without lysing nuclear membranes. The sample preparation region also comprises an elution buffer storage device for storing an elution buffer. The sample preparation region further comprises a sample card having multiple chambers for receiving the patient sample. Each chamber comprises an inlet, a filter and an outlet. The sample card is removably insertable into said sample preparation region of said microfluidic device. The sample preparation region also comprises a flow control system for controlling flow of the lysis buffer and the elution buffer to each chamber of said sample card. The flow control system controlling the flow of lysis buffer into each chamber of the sample card such that the lysis buffer selectively lyses cellular membranes to release nuclei and cell debris causing the cell debris to flow through the filter into a waste receptacle positionable beneath the sample card and without lysing nuclear membranes of nuclei in the patient sample which become trapped on the filter. The sample preparation region further comprises a temperature control system for heating the filter in the sample card sufficient to lyse nuclei trapped on said filter and release DNA. The sample preparation region also comprises an interface chip comprising multiple DNA sample wells and DNA sample outlets, wherein said interface chip is positionable beneath the sample card and is configured to receive the DNA released from the lysed nuclei trapped on said filter. The microfluidic system further comprises a main controller in communication with the temperature control system, the flow control system, and the microfluidic chip. In one embodiment, the main controller controls the flow of DNA from the interface chip to the amplification region and/or the detection region of the microfluidic chip.

In some embodiments, the temperature control system comprises a heating source and a heat sensor. In other embodiments, the flow control system comprises a pump and a solution delivery chip in which the solution delivery chip comprises multiple channels for delivering lysis buffer and elution buffer to each chamber of the sample card. In some embodiments, the multiple chambers of the sample card are in fluid communication. In other embodiments, the flow control system further comprises a pressure control system, wherein the pressure control system comprises an air source, a pressure sensor for controlling the delivery of the elution buffer and the lysis buffer to each chamber of the sample card. In some embodiments, the multiple chambers of the sample card are in fluid communication in which a patient sample in one chamber can be driven into other chambers. In other embodiments, the sample card is disposable.

In another aspect, the present invention provides a method for isolating DNA from cells in a patient sample. In accordance with this aspect, the method comprises providing a microfluidic system comprising (i) a sample card having multiple chambers for receiving the patient sample, wherein each chamber comprises an inlet, a filter and an outlet, said sample card being removably insertable into said microfluidic system, (ii) a flow control system for controlling flow of a lysis buffer and an elution buffer to each chamber of the sample card, (iii) a temperature control system for heating the filter in the sample card; (iv) a waste receptacle positionable beneath the sample card, and (v) an interface chip comprising multiple DNA sample wells and DNA sample outlets, wherein said interface chip is positionable beneath the sample card.

The method also comprises loading the patient sample into the chambers of the sample card. The method further comprises inserting the sample card into the microfluidic system. The method also comprises delivering lysis buffer to the chamber of the sample card and selectively lysing cellular membranes of the patient sample without lysing nuclear membranes of nuclei, producing a solution comprising lysis buffer, intact nuclei and cellular debris. The method further comprises controlling the flow control system to drive the lysis buffer and the cellular debris through the filter and into the waste receptacle, thereby trapping the intact nuclei on the filter. The method also comprises controlling the temperature control system to heat the filter causing the intact nuclei trapped on the filter to lyse, thereby releasing DNA. The method further comprises delivering an elution buffer to the chambers of the sample card. The method also comprises controlling the flow control system to drive the elution buffer and the DNA to the DNA sample wells in the interface chip. In some embodiments, the lysis buffer is repeatedly delivered to the chambers of the sample card to clean the filters.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

FIG. 8 illustrates a top view of layer 3 of the microfluidic sample preparation device of FIG. 4.

FIG. 9 is a longitudinal cross-sectional view of layer 3 of the microfluidic sample preparation device of FIG. 4.

FIG. 10 illustrates a top view of layer 4 of the microfluidic sample preparation device of FIG. 4.

FIG. 11 is a longitudinal cross-sectional view of layer 4 of the microfluidic sample preparation device of FIG. 4.

FIG. 15A shows the membrane before trapping the nuclei. FIG. 15B shows the membrane after trapping the nuclei which are dyed with a fluorescence dye.

DETAILED DESCRIPTION OF PREFERRED EMBODIMENTS

Figure 1:
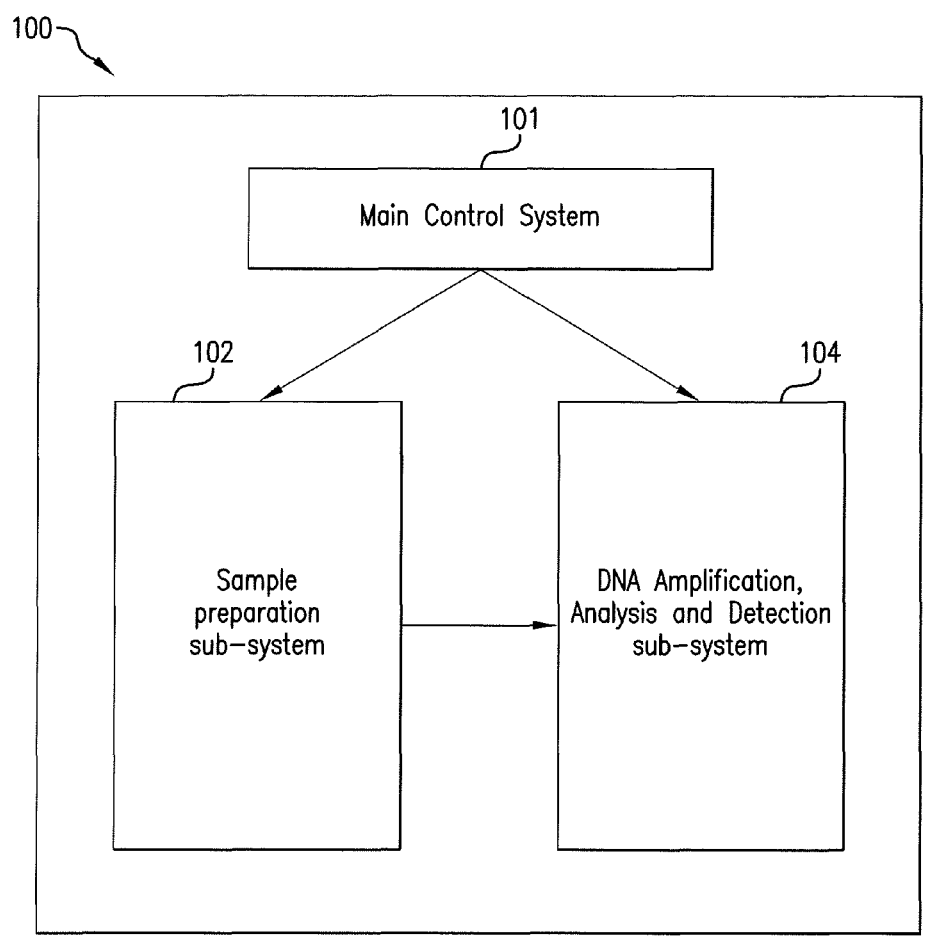
FIG. 1 is a functional block diagram of a DNA preparation and analysis system.

FIG. 1 illustrates a microfluidic DNA analysis system 100 according to some embodiments of the invention. As illustrated in FIG. 1, system 100 includes a DNA sample preparation sub-system 102 (a.k.a., "the sample preparation unit"), a DNA amplification, analysis and detection subsystem 104, and a main control system 101. The present application is primarily directed to the sample preparation unit 102 and earlier filed applications describe various embodiments of subsystem 104 (see e.g., U.S. Pat. Pub. Nos. 2008/0003588, 2008/0130971, 2008/0176230, and 2009/0053726, all of which are incorporated herein in their entirety by this reference).

Figure 2:
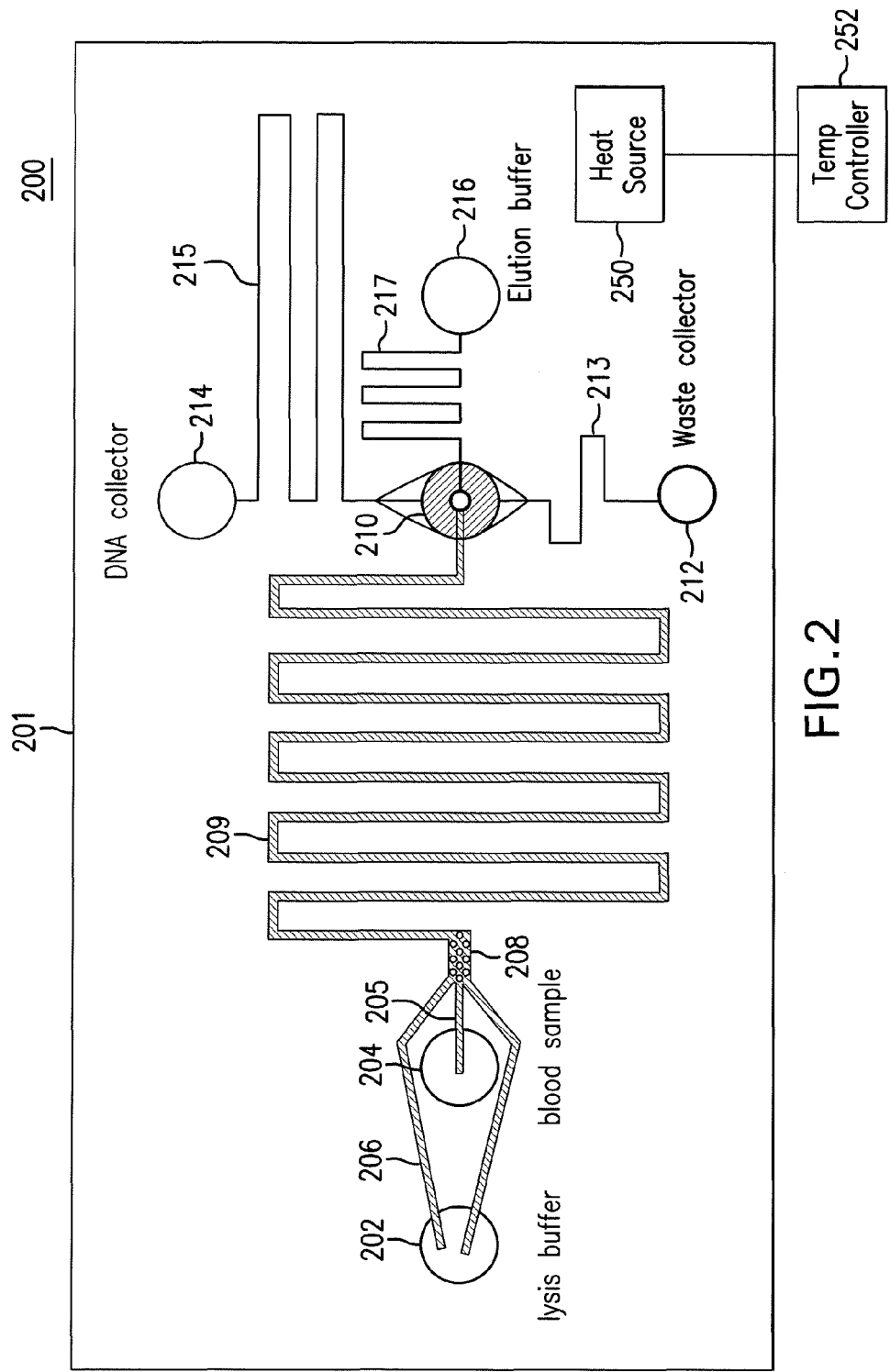
FIG. 2 shows a schematic illustration of a microfluidic DNA sample preparation device in accordance with an embodiment of the invention.

FIG. 2 shows a schematic illustration of a component 200 of sample preparation unit 102 in accordance with an embodiment of the invention. More specifically, FIG. 2 shows a schematic illustration of a microfluidic DNA sample preparation device 200. As illustrated in FIG. 2, device 200 comprises a chip 201, a well 202 formed in chip 201 for storing a lysis buffer, and one or more microfluidic channels 206 formed in chip 201 that fluidly connect well 202 to a mixing region 208 formed in chip 201, thereby providing a path for the lysis buffer in well 202 to travel to the mixing region 208. Device 200 also includes a sample well 204 formed in chip 201 for storing a sample to analyzed (e.g., a blood sample). Like well 202, well 204 is connected in fluid communication with mixing region 208 via one or more channels 205 formed in chip 201.

Figure 15A:
FIGS. 15A and 15B show trapping of nucleic by the membrane.
Figure 15B:
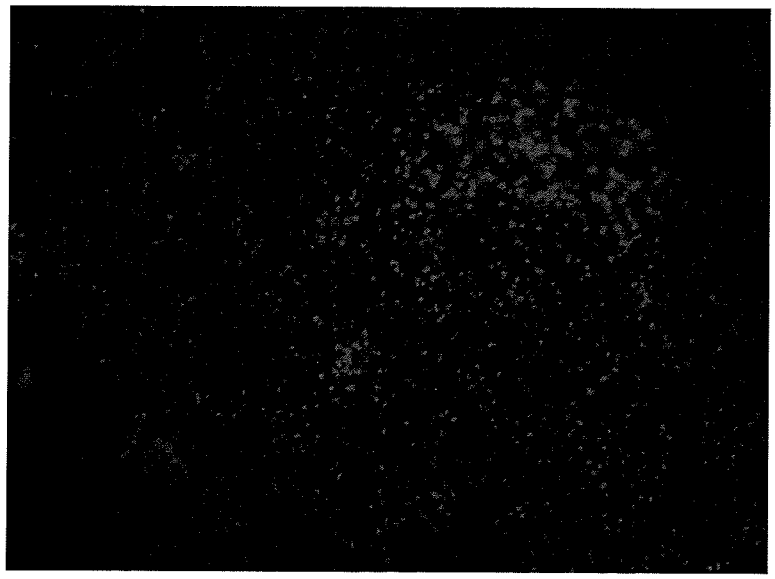

Mixing region 208 is configured to permit a sample from well 204 and lysis buffer from well 202 to mix. Mixing region 208, which my simply be a small channel, is connected in fluid communication with a filter 210 (e.g., a permeable membrane or other filter) disposed in chip 201 via a microfluidic channel 209 formed in chip 201. In some embodiments, filter 210 is made of any combination of one or more of the following: silicon, glass, polymers, polyester, polycarbonate, and nitrocellulose. Filter 210 may have a round shape, rectangular shape, or other shape. In some embodiments, filter 210 comprises a number of pores and the pore sizes may range from 500 nanometers (nm) to 10 micrometers (um). For example, in some embodiments, the pore sizes range from approximately 0.5 um to 10 um. FIGS. 15a and 15b illustrate an exemplary embodiment of filter 210.

Channel 209 is configured to function as a cell lysis region. That is, channel 209 is configured to permit the lysis buffer from well 202 to selectively lyse cellular membranes of cells in the patient sample from well 204 without lysing nuclear membranes of the cells to produce intact nuclei from the cells in the patient sample. For example, in the cell lysis region red blood cells may be disrupted before reaching the filter 210 while white blood cells are partially lysed such that nuclei are intact when the mixture reaches filter 210.

As further shown in FIG. 2, a waste well 212, a DNA collection well 214, and an elution buffer well 216 are also formed in chip 201. Additionally, each of the wells 212, 214 and 216 are connected in fluid communication with filter 210 via microfluidic channels 213, 215 and 217, respectively. In some embodiments, during use, well 216 stores an elution buffer which can be, for example, a Tris buffer, KCl and/or a zwitterion. Main control system 101, as illustrated in FIG. 1, can cause the elution buffer to flow into filter 210.

During use of chip 200, filter 210 forms a nuclei trapping region wherein the intact nuclei from the sample are trapped by filter 210 while other components of the patient sample flow through filter 210 and into waste collection region 212. Filter 210 also functions as a nuclei lysis region in which the nuclear membranes of the intact nuclei are lysed to release the DNA. The released DNA is forced to flow to DNA collection region 214.

As further shown in FIG. 2, device 200 may include a heat source 250. Heat source 250 may be formed in or on chip 201 or may be structurally separate from chip 201. Heat source 250 may be an electrical heater (i.e., a device that converts electrical energy into heat) or other type of heat producer. Heat source 250 may be controlled by a temperature controller 252, which may be a module of main controller 101 or a separate component that is in communication with main controller 101. Heat source 250 is controlled, configured and arranged to transfer heat to filter 210 at desired times. For example, when intact nuclei are trapped by filter 210, heat source 250 may be controlled to cause the transfer of heat to filter 210, which heat is preferably sufficient to lyse or facilitate the lysing of the nuclear membranes of the nuclei, thereby releasing the DNA contained by the nuclear membranes.

Figure 3A:
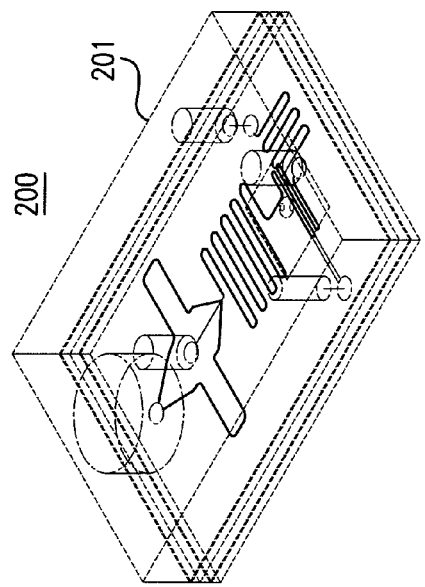
FIG. 3A illustrates a multi-layered microfluidic sample preparation device in accordance with an embodiment of the invention.
Figure 3C:
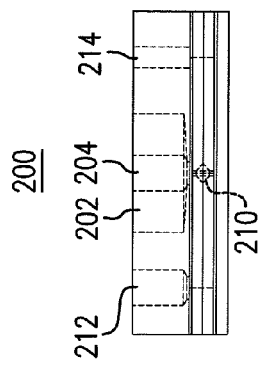
FIG. 3C is a transverse cross-sectional view of a multi-layered microfluidic sample preparation device in accordance with an embodiment of the invention.
Figure 3B:
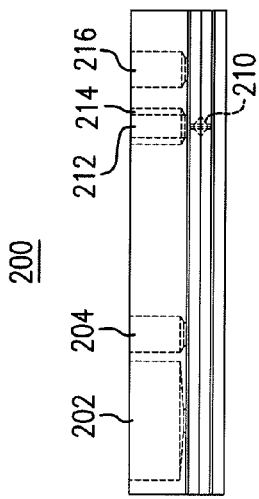
FIG. 3B is a longitudinal cross-sectional view of a multi-layered microfluidic sample preparation device in accordance with an embodiment of the invention.

In some embodiments, chip 201 is a multilayer chip. That is, chip 201 may comprise two or more boards. Referring now to FIGS. 3A-3C, a multilayered embodiment of device 200 is illustrated. In the non-limiting embodiment illustrated in FIG. 3A, device 200 includes six layers. However, fewer or more layers also could be used. FIG. 3B shows a longitudinal cross-sectional view of device 200 in accordance with the embodiment shown in FIG. 3A, and FIG. 3C shows a transverse cross-sectional view of device 200 in accordance with the embodiment shown in FIG. 3A.

Figure 4:
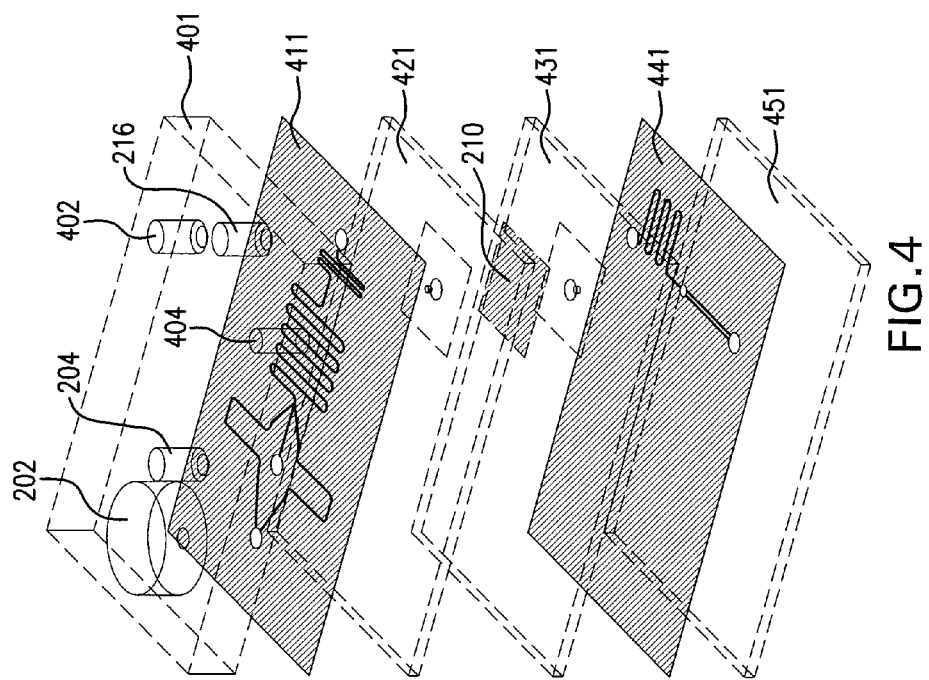
FIG. 4 is an exploded view of a multi-layered microfluidic sample preparation device in accordance with an embodiment of the invention.
Figure 5:
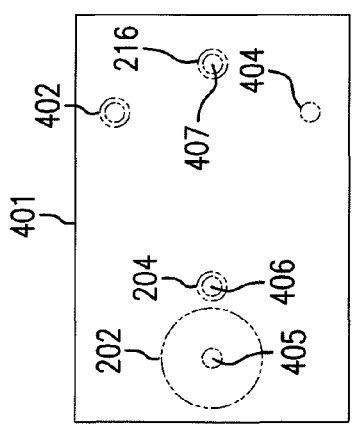
FIG. 5 illustrates a top view of layer 1 of the microfluidic sample preparation device of FIG. 4.

FIG. 4 illustrates an exploded view of the embodiment of device 200 shown in FIG. 3A. In the first layer (or top layer) 401, a top view of which is shown in FIG. 5, wells 202, 204 and 216 are formed for containing the lysis buffer, sample and elution buffer, respectively. Also formed in layer 401 is a through hole 402 in fluid communication with DNA collector well 214 and a through hole 404 in fluid communication with waste well 212. In one non-limiting embodiment, layer 401 is preferably approximately five (5) millimeters thick and is made from Poly(methyl methacrylate) (PMMA). Other thicknesses and materials also may be used for this layer in additional embodiments.

Figure 6:
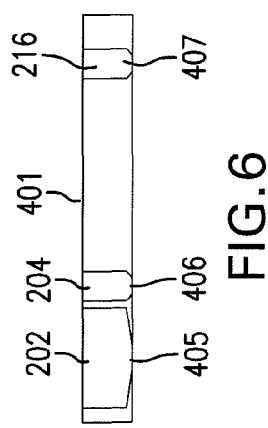
FIG. 6 is a longitudinal cross-sectional view of layer 1 of the microfluidic sample preparation device of FIG. 4.

As further shown in FIG. 5 and FIG. 6, which is a longitudinal cross sectional view of layer 401, well 202 has a port 405 in its bottom surface so that fluid can flow from well into channels 206. Likewise, well 204 has a port 406 in its bottom surface so that fluid can flow from well 204 into channel 205. Thus, ports 405 and 406 are in fluid communication with mixing region 208. Similarly, well 216 has port 407 in its bottom surface so that fluid can flow from well 216 into channel 217. As shown in FIG. 4, channels 205, 206 and 217 are formed in the second layer 411 of device 200.

Figure 7:
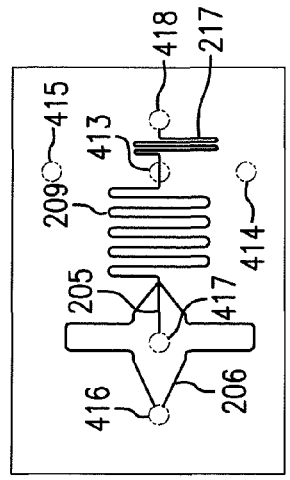
FIG. 7 illustrates a top view of layer 2 of the microfluidic sample preparation device of FIG. 4.

FIG. 7 illustrates a top view of second layer 411. As shown in FIG. 7, formed in second layer 411 are a mixing region 208, channel 209, through holes 413, 414 and 415, and closed bottom wells 416, 417, and 418. Channel 209 fluidly connects mixing region 208 with hole 413 so that a lysis buffer and sample mixture, which may be formed in mixing region 208, can flow into hole 413 and down to the third layer 421 of device 200. Likewise, channel 217 connects well 418, which is positioned directly beneath hole 407 of elution buffer well 216, with hole 413 so that elution buffer can flow from well 216 into hole 413 and down to the third layer of device 200. Through hole 414 is positioned beneath through hole 404 so that fluid may flow through hole 414 into hole 404, and through hole 415 is positioned beneath through hole 402 so that fluid may flow through hole 415 into hole 402. In one non-limiting embodiment, the second layer 411 of device 200 may comprise a 150 micrometer thick cyclic olefin copolymer (COC) film. Other thicknesses and materials also may be used for this layer in additional embodiments.

FIG. 8 illustrates a top view of third layer 421 which includes through holes 422, 423 and 424. Through hole 422 is positioned beneath through hole 414 so that fluid may flow through hole 422 into hole 414, through hole 423 is positioned beneath through hole 413, so that fluid may flow through hole 413 into hole 423, and through hole 424 is positioned beneath through hole 415 so that fluid may flow through hole 423 into hole 415. FIG. 9 shows a longitudinal cross-sectional view of layer 421. In one non-limiting example, the third layer 421 of device 200 may comprise a 1 millimeter thick PMMA board. Other thicknesses and materials also may be used for this layer in additional embodiments.

FIG. 10 illustrates a top view of fourth layer 431 which includes through holes 432, 433 and 434. Through hole 432 is positioned beneath through hole 422 so that fluid may flow through hole 432 into hole 422, through hole 433 is positioned beneath through hole 423, so that fluid may flow through hole 423 into hole 433, and through hole 434 is positioned beneath through hole 424 so that fluid may flow through hole 434 into hole 424. FIG. 11 shows a longitudinal cross-sectional view of layer 421. In one non-limiting embodiment, the fourth layer 431 of device 200 may comprise a 1 millimeter thick PMMA board. Other thicknesses and materials also may be used for this layer in additional embodiments.

As shown in FIG. 4, filter 210 is sandwiched between the third and fourth layers of device 200. In some embodiments, filter 210 may be made of any combination of one or more of silicon, glass, polymers, polyester, polycarbonate, and nitrocellulose, as described above. In one non-limiting embodiment, filter 210 is approximately 9 mm by 9 mm and has a thickness of approximately 10 μm. The filter may have other thicknesses and dimensions in additional embodiments.

Figure 13:
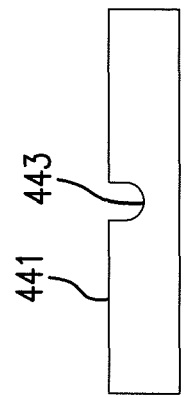
FIG. 13 is a longitudinal cross-sectional view of layer 5 of the microfluidic sample preparation device of FIG. 4.
Figure 12:
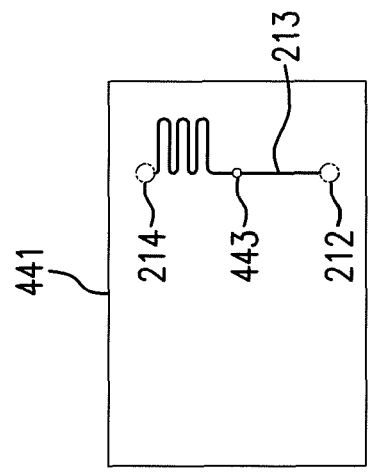
FIG. 12 illustrates a top view of layer 5 of the microfluidic sample preparation device of FIG. 4.

FIG. 12 illustrates a top view of fifth layer 441. As shown in that figure, closed bottom wells 212, 443 and 214 are formed on the top surface of layer 441. Also, microfluidic channel 215 is formed on the top surface of layer 441 as well as channel 213, which connects well 443 with waste collection well 212. Closed bottom wells 212, 443, and 214 are positioned beneath through holes 432, 433, 434, respectively. FIG. 13 shows a longitudinal cross-sectional view of layer 441. On one non-limiting embodiment, the fifth layer 441 of device 200 may comprise a 150 micrometer thick COC film. Other thicknesses and materials also may be used for this layer in additional embodiments.

As illustrated in FIG. 4, the sixth layer of device 200 is a base layer 451. In one non-limiting embodiment, layer 451 may comprise a 1 millimeter thick board made of PMMA. Other thicknesses and materials also may be used for this layer in additional embodiments. In some embodiments, the third, fourth and sixth layers are removed, thereby creating a three layer device.

Figure 14:
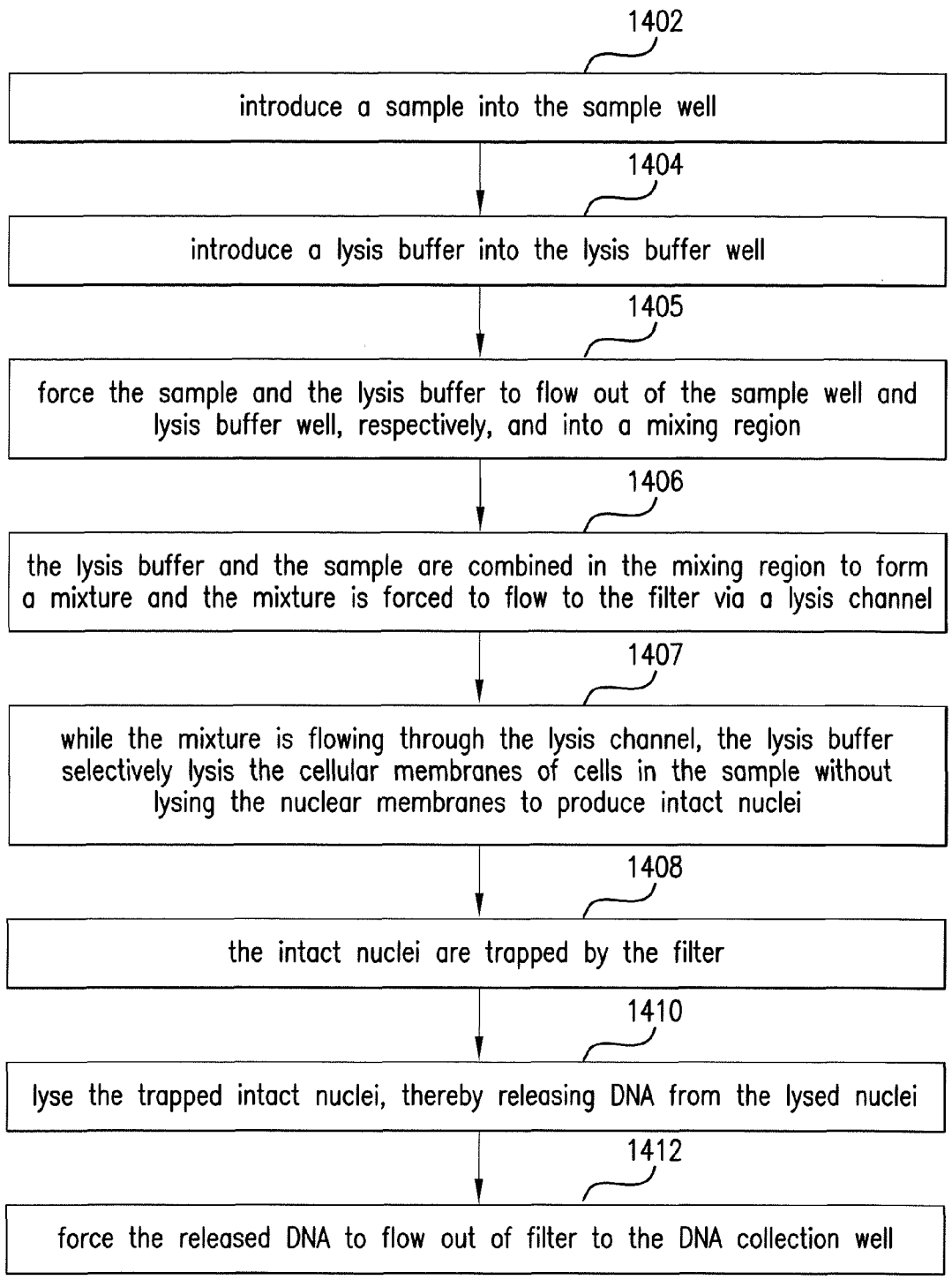
FIG. 14 is a flow chart illustrating a process according to an embodiment of the invention.

Referring now to FIG. 14, a flow chart illustrating a process 1400 for preparing DNA for analysis using device 200 is shown. Process 1400 may begin in step 1402, where a sample (e.g., a sample of blood containing white blood cells) is introduced into sample well 204. In step 1404, a lysis buffer is introduced into lysis buffer well 202. In step 1405, the lysis buffer is forced to flow out of well 202 through port 405 and channel 206 into mixing region 208. At or about the same time, the sample is forced to flow out of sample well 204 through port 406 and channel 205 into mixing region 208. In step 1406, the lysis buffer and sample mix in the mixing region 208 and the mixture is forced to flow to filter 210 via channel 209. In embodiments where the sample contains white blood cells, the sample may be enriched for white blood cells prior to introducing the sample into mixing region 208.

While the lysis buffer/patient sample mixture is in channel 209 and travelling towards filter 210, the lysis buffer selectively lyses the cellular membranes of cells in the patient sample without lysing the nuclear membranes of cells to produce intact nuclei from the cells, as reflected in step 1407. When the mixture reaches filter 210, the mixture preferably contains released intact nuclei from the patient sample. In step 1408, the intact nuclei are trapped by filter 210 while the waste (i.e., other components of the sample and lysis buffer) passes through filter 210 and is forced to travel via channel 213 to waste collection well 212.

In step 1410, the intact nuclei trapped on filter 210 are lysed, thereby releasing DNA from the lysed nuclei. In some embodiments, the step of lysing the intact nuclei comprises causing an elution buffer in well 216 to flow to filter 210 via channel 217 and/or heating the trapped nuclei using heater 250. In some embodiments, the elution buffer comprises a Tris buffer, KCl and/or a zwitterion. In some embodiments, the elution buffer is an amplification reaction buffer. In embodiments where heat is used to lyse the trapped nuclei, the trapped nuclei may be heated at a temperature in the range of approximately 35 degrees centigrade to 95 degrees centigrade for approximately 1 to 10 minutes. For example, in one embodiment, the trapped nuclei may be heated at a temperature in the range of approximately 50 degrees centigrade for approximately 7 minutes.

In step 1412, after lysing the intact, trapped nuclei, the DNA released from the nuclei is collected in the DNA collection well 214. For example, the released DNA flows out of filter 210 and to well 214 via channel 215. In some embodiments, the released DNA flows to well 214 by flowing an elution buffer from well 216 such that the elution buffer flows out of port 407 and into channel 217, then through channel 217 to and through the filter 210 where the released DNA mixes with the elution buffer, and then flows through channel 215 into well 214. Once in well 214, the mixture containing the released DNA and elution buffer can be removed from chip 201 via through holes 402, 415, 424, and 434, all of which are in fluid communication with well 214.

While not shown, it is well known in the art that device 200 may be coupled to a flow control system (e.g., a system that comprises one or more pumps) for causing the various buffers, samples and mixtures to flow as described above. Additionally, device 200 may be coupled with a microfluidic platform. The DNA purified by device 200 may be directly delivered by a pump to a well in the microfluidic platform, and further mix with other PCR components.

FIGS. 15A and 15B show trapping of nucleic acid by the membrane in accordance with an embodiment of the present invention. Specifically, FIG. 15A shows fluorescence emitted from membrane prior to the membrane trapping dye stained nuclei, and FIG. 15B fluorescence emitted from membrane after the membrane has trapped dye stained nuclei.

Figure 16:
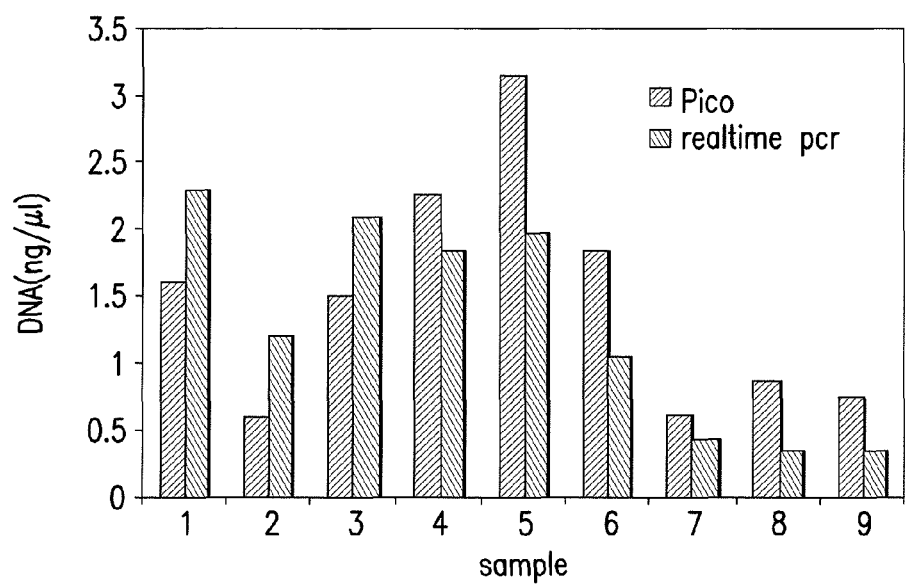
FIG. 16 is a graph showing the results of an experiment.

Referring now to FIG. 16, a graph is provided showing results achieved from using an above-described method. In particular, DNA purification was tested using 9 patient blood samples. After obtaining purified DNA using this method, one fraction of purified DNA sample was quantified by Pico green method (fluorescence based method for measuring total DNA concentration). Another fraction of purified DNA sample was quantified by real time-PCR. The results show that real time-PCR result is comparable to Pico green assay, indicating that no significant amount of inhibits exist in the purified DNA sample.

The table below provides representative dimensions for many of the above described components of device 200. These dimensions are illustrative and not intended to be limiting in any way.

TABLE 1

| Component | Dimensions |
| --- | --- |
| chip 201 | length: 42 mm; width: 28 mm; height: 8.3 mm |
| channel 206 | length: 28 mm; width: 150 μm; depth: 150 μm |
| channel 205 | length: 5.4 mm; width: 100 μm; depth: 150 μm |
| channel 209 | length: 100 mm; width: 200 μm; depth: 150 μm |
| channel 213 | length: 7.75 mm; width: 400 μm; depth: 150 μm |
| channel 215 | length: 42 mm; width: 100 μm; depth: 150 μm |
| channel 217 | length: 36 mm; width: 100 μm; depth: 150 μm |

Figure 17:
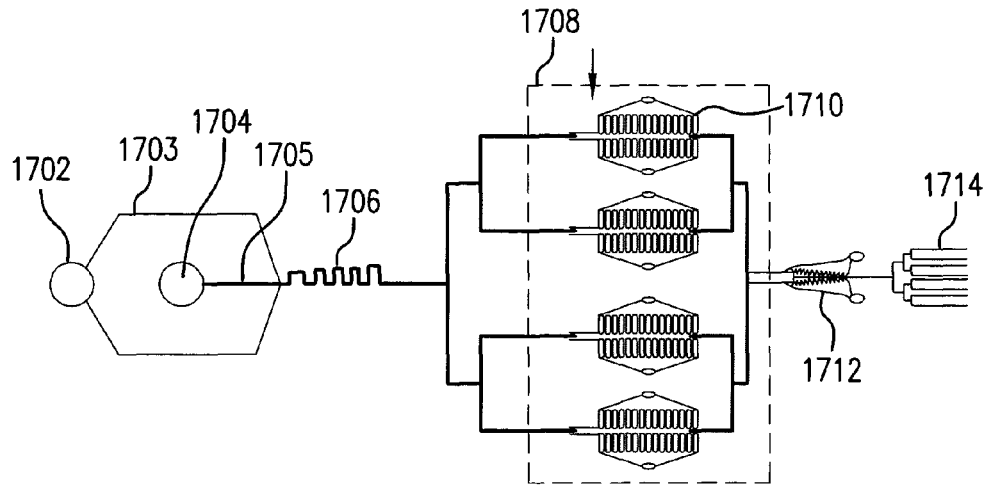
FIG. 17 shows a schematic illustration of a cross-flow microfluidic device for sample preparation in accordance with other embodiments of the present invention.

Referring now to FIG. 17, a schematic illustration is provided of various components of sample a preparation subsystem 102 according to other embodiments of the present invention. As shown in FIG. 17, system 102 may include a sample well 1702 for containing a sample (e.g., a sample of blood containing white and red blood cells), a lysis buffer well 1704 for containing a lysis buffer, and a channel 1706 in fluid communication with wells 1702 and 1704 via channels 1703 and 1705, respectively. Channel 1706 may function as a cell lysis region. That is, channel 1706 may be configured such that the lysis buffer from well 1702 is permitted to mix with the sample from sample well 1704 resulting in the selective lysing of cellular membranes of cells in the sample without lysing nuclear membranes of the cells to produce intact nuclei from the cells in the sample.

As further shown in FIG. 17, system 102 may include a cross-flow filtration region 1708 in fluid communication with channel 1706. In some embodiments, in region 1708 intact nuclei (or white cells or other target components) are separated from other components of the sample (e.g., proteins and other PCR inhibitors) by one or more cross-flow filters 1710, each having a pore size such that the target components (e.g., intact nuclei) are prevented from being carried away by a cross-flow buffer that is controlled to flow through the cross-flow filtration region, but other components of the patient sample flow through filters and are carried away by the cross-flow buffer. In the non-limiting embodiment shown in FIG. 17, cross-flow filtration region 1708 includes four cross flow filters 1710 that are connected in parallel. In other embodiments, region 1708 may have one, two, three or five or more filters 1710. Additionally, in some embodiments, some filters 1710 may be arranged in series. Moreover, each filter 1710 may have a different average pore size.

System 102 may also include a concentrator region 1712, which is in fluid communication with cross flow filtration region 1708, in which the intact nuclei from the cross-flow filtration region are concentrated. An interface region 1714 may be in fluid communication with concentrator 1712. As will be explained herein, purified intact nuclei preferably exit concentrator 1712 and enter interface region 1714, which includes one or more interface channels through which purified nuclei flow for downstream processing and analysis.

Figure 18:
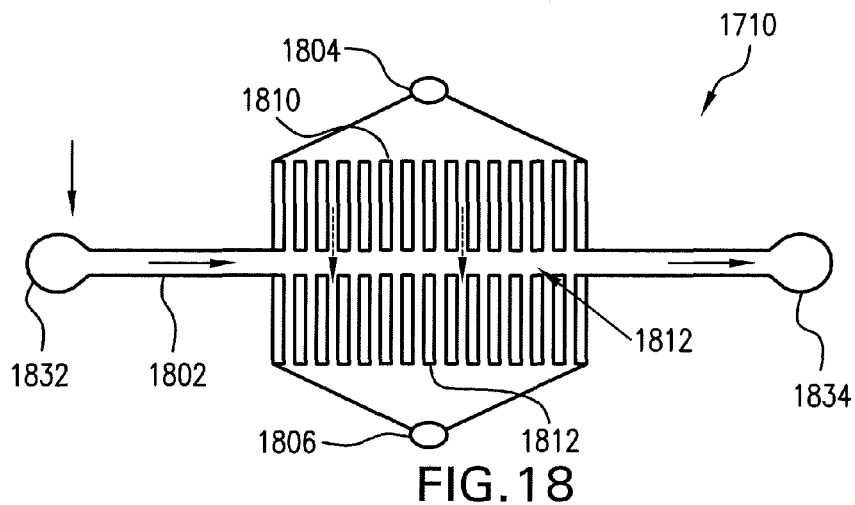
FIG. 18 shows a schematic illustration of a cross-flow filter in accordance with an embodiment of the present invention.

FIG. 18 further illustrates an embodiment of cross-flow filter 1710. As shown in FIG. 18, cross-flow filter 1710 includes a microfluidic separation channel 1802, which, as shown in FIG. 17, is in fluid communication with the cell lysis region 1706 and concentrator 1712. Channel 1802 is configured such that fluid entering channel 1802 from channel 1706 can flow through channel 1802 such that the fluid will reach and enter the concentration region 1712. A filter 1810 and a filter 1812 are disposed in a middle portion of channel 1802. Filters 1810 and 1812 are arranged to form a separation chamber 1814.

In operation, while the lysis buffer/sample mixture is flowing through channel 1802 (i.e., from the input end 1832 to the output end 1834), a cross-flow fluid is introduced into the portion of channel 1802 having the filters 1810 and 1812 via a cross-flow buffer input port 1804. The cross-flow fluid exits this portion of the channel 1802 via a cross-flow buffer output port 1806. Advantageously, there is a differential (e.g., a pressure differential or voltage differential, such as an electrophoretic voltage potential, or a gravitational field) between ports 1804 and 1806 that causes the cross-flow fluid that enters channel 1802 via port 1804 to flow first through filter 1810, then through separation chamber 1814, then through filter 1812, and finally out of channel 1802 via exit port 1806. There is also a force (e.g., pressure, electric, gravity) that causes fluid entering channel 1802 to flow from end 1832 to end 1834. As the cross-flow buffer flows across separation chamber 1814 (as illustrated by the dashed lines), the cross-flow buffer together with filters 1810 and 1812 facilitate the separation of the intact nuclei from the other components of the mixture that flows into channel 1802 from cell lysis region 1706. More specifically, the pore size of the filters 1812 and 1810 are such that the intact nuclei do not pass through filter 1812, but are driven toward the concentrator region 1712 by the flow of fluid from end 1832 to end 1834, whereas other, smaller components of the sample are driven through filter 1812 and driven towards exit port 1806 via the cross-flow of the cross-flow buffer. In this manner, intact nuclei (or other target material) can be efficiently separated from the other components of the sample. Preferably, one type of force (e.g., air pressure) is used to cause fluid entering channel 1802 to flow from end 1832 to end 1834, while a different type of force (e.g. an electrical field, gravity) is used to cause the cross-flow fluid to flow from 1804 to 1806.

In some embodiments, the size of the pores of filters 1810 and 1812 is between approximately 1 um and 15 um. For example, the size of the pores of filter 1812 may be about 5 um. In some embodiments, filters 1810 and 1812 may consists of or include a membrane and/or an array of pillars.

Figure 19:
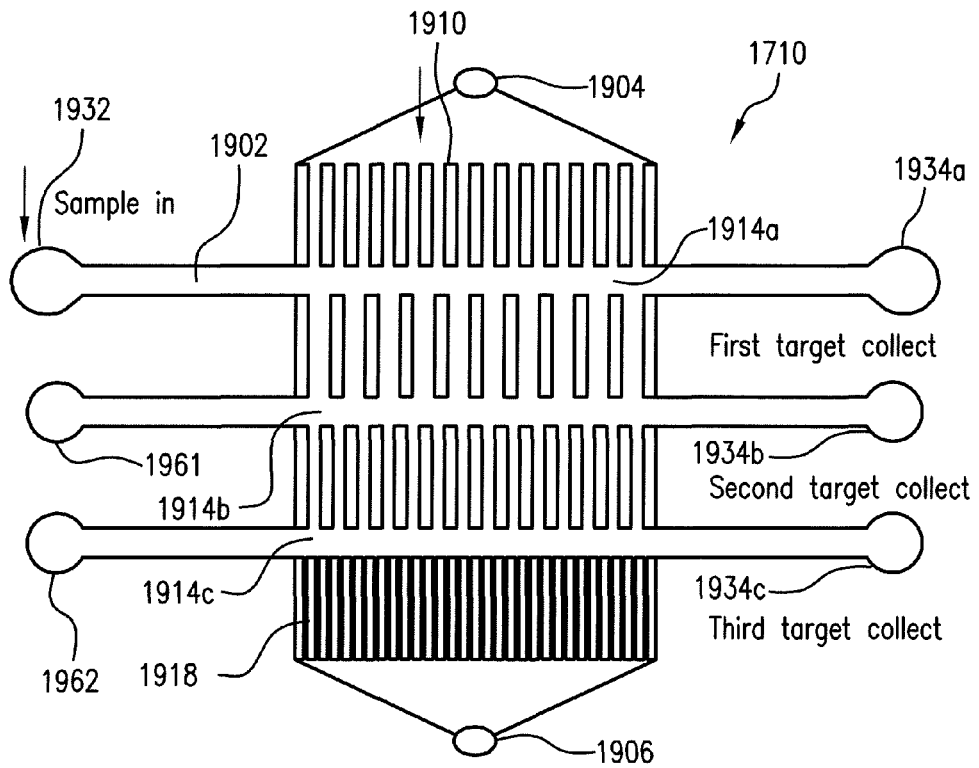
FIG. 19 shows a schematic illustration of a cross-flow filter in accordance with other embodiments of the present invention.

Referring now to FIG. 19, a cross-flow filter 1710 according to another embodiment is illustrated. As shown in FIG. 19, cross-flow filter 1710 may include a microfluidic separation channel 1902. In an exemplary embodiment, filters 1910, 1912, 1916, and 1918 are disposed in a middle portion of channel 1902. Filters 1910, 1912, 1916, and 1918 are arranged to form separation chambers 1914a, 1914b, and 1914c.

In operation, while the lysis buffer/sample mixture is flowing through channel 1902 (e.g., from the input end 1932 towards an output end 1934a), a cross-flow fluid is introduced into the portion of channel 1902 having the filters via a cross-flow buffer input port 1904. The cross-flow fluid exits the portion of channel 1902 having the filters via a cross-flow buffer output port 1906. Advantageously, there is a differential (e.g., a pressure differential or voltage differential, such as an electrophoretic voltage potential) between ports 1904 and 1906 that causes the cross-flow fluid that enters channel 1902 via port 1904 to flow first through filter 1910, then through separation chamber 1914a, then through filter 1912, then through separation chamber 1914b, then through filter 1916, then through separation chamber 1914c, then through filter 1918, and finally out of channel 1902 via exit port 1906. There is also a differential (e.g., pressure or electric) that causes fluid entering separation chambers 1914a, 1914b, and 1914c to flow towards ends 1934a, 1934b, and 1934c, respectively. As the cross-flow buffer flows across a separation chamber 1914a, the cross-flow buffer together with the filters that form the separation chamber 1914a facilitate the separation of desired components (e.g., intact nuclei, bacteria, viruses) from the other components of the mixture that flows into the separation chamber.

More specifically, for example, the pore size of the filters 1912 and 1910 are such that the intact nuclei do not pass through filter 1912, but are driven toward end 1934 by a differential, whereas other, smaller components of the sample (e.g., bacteria, viruses or waste material) are driven through filter 1912 and into separation chamber 1914b by the flow of the cross-flow buffer. For example, the average pore size of filter 1912 may be between approximately 1 um and 15 um. In one embodiment, the average pore size is about 8 um.

The pore size of the filter 1916 may be such that bacteria does not pass through filter 1916, but are driven toward end 1934b by a differential, whereas other, smaller components of the sample (e.g., viruses) are driven through filter 1916 into separation chamber 1914c by the flow of the cross-flow fluid. For example, the average pore size of filter 1916 may be between approximately 0.2 um and 2 um. In one embodiment, the average pore size is about 0.4 um. The pore size of the filter 1918 may be such that viruses do not pass through filter 1918, but are driven toward end 1934*c* by a differential, whereas other, smaller components of the sample are driven through filter 1918 and driven towards exit port 1906 via the cross-flow of the cross-flow buffer. For example, the average pore size of filter 1918 may be between approximately 10 nm 400 nm. In one embodiment, the average pore size is about 100 nm. Port 1961 may be used to create a pressure differential between port 1961 and end 1934*b* so that a fluid in chamber 1914*b* will flow towards end 1934*b*. Likewise, Port 1962 may be used to create a pressure differential between port 1962 and end 1934*c* so that a fluid in chamber 1914*c* will flow towards end 1934*c*.

In the above manner, intact nuclei, bacteria and viruses may be separated from the sample collected in separate target collection ports using the cross flow filter 1710 as illustrated in FIG. 19, in accordance with one embodiment.

Figure 20:
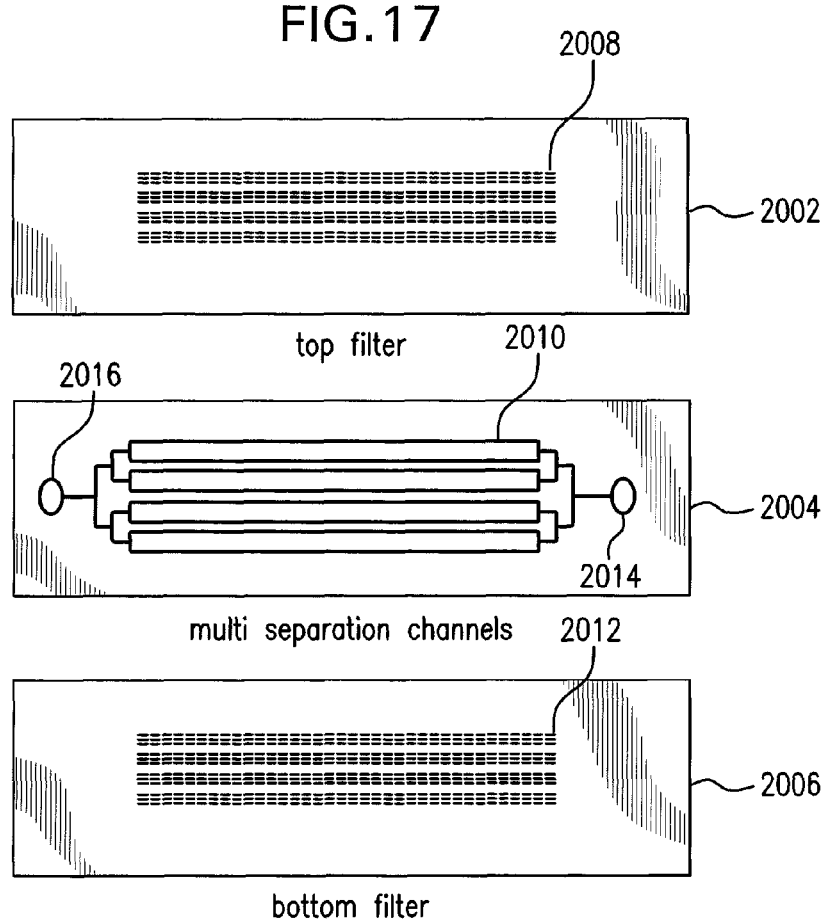
FIG. 20 shows a schematic illustration of a cross-flow microfluidic device for sample preparation in accordance with further embodiments of the present invention.
Figure 21:
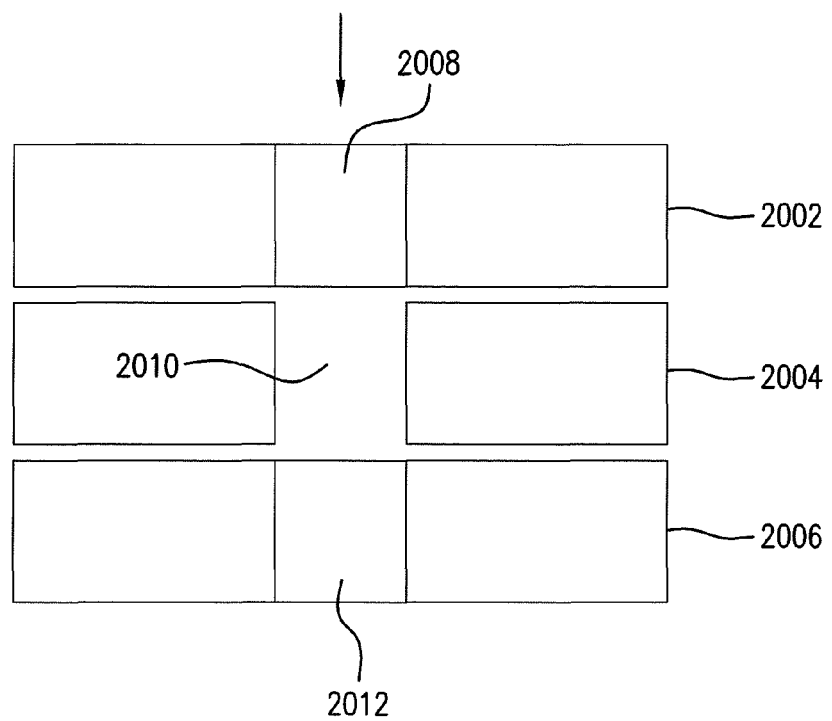
FIG. 21 is a transverse cross-sectional view of the cross-flow microfluidic device shown in FIG. 20.

Referring now to FIG. 20, a layered embodiment of filter 1710 in illustrated. As shown in FIG. 20, a filter 1710 may include three layers: a top layer 2002, a middle layer 2004, and a bottom layer 2006. A filter 2008 may be formed in top layer 2002, one or more separation channels 2010 may be formed in middle layer 2004, and a filter 2012 may be formed in bottom layer 2006. At least a portion of the separation channel 2010 extends from the top surface of layer 2004 to the bottom surface of layer 2004, as shown in FIG. 21, which shows a cross sectional view of this embodiment of filter 1710. As shown in FIG. 21, layer 2002 is positioned on top of layer 2004 such that filter 2008 is on top of channel 2010, thereby forming a top, porous wall of channel 2010. Likewise, as shown in FIG. 21, layer 2006 is positioned beneath layer 2004 such that filter 2012 is underneath channel 2010, thereby forming a bottom, porous wall of channel 2010.

In operation, while the lysis buffer/sample mixture is flowing through channels 2010 (i.e., from the input end 2006 to the output end 2014), a cross-flow fluid is introduced into the portion of channel 2010 having the filters 2008 and 2012 via a cross-flow buffer input port (not shown). The cross-flow fluid exits this portion of the channel 2010 via a cross-flow buffer output port (also not shown). As with previous embodiments, there is a differential (e.g., a pressure differential or voltage differential, such as an electrophoretic voltage potential, or a gravitational field) between the cross-flow buffer input and output ports that causes the cross-flow fluid that enters channel 2010 to flow first through filter 2008, then through the separation chamber, then through filter 2012, and finally out of channel via the exit port. There is also a force (e.g., pressure, electric, gravity) that causes fluid entering channel 2010 to flow from end 2006 to end 2014. As with previous embodiments, as the cross-flow buffer flows across separation chamber, the cross-flow buffer together with filters 2008 and 2012 facilitate the separation of the intact nuclei from the other components of the mixture that flows into channel 2010 from, for example, the cell lysis region 1706.

Figure 22:
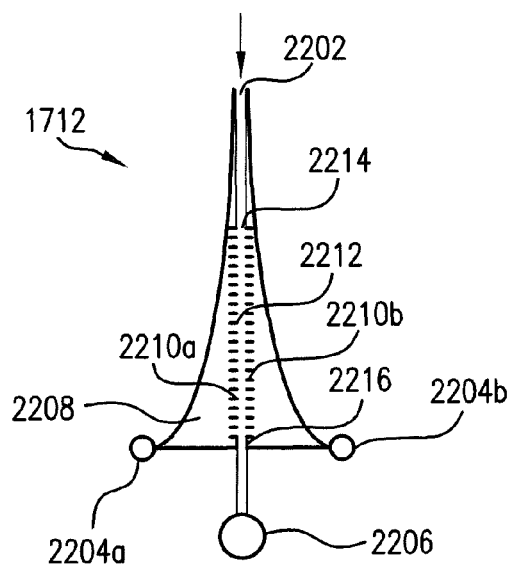
FIG. 22 illustrates a sample concentrator in accordance with embodiments of the present invention.

Referring back to FIG. 17, as described above, system 102 may include a concentrator 1712, as further illustrated in FIG. 22. As shown in FIG. 22, a concentrator 1712, in accordance with one exemplary embodiment, includes a generally triangular shaped channel 2208 (i.e., a channel wherein the width of the channel increases as one moves from an input end to an output end). At the input end of channel 2208 there is an inlet 2202 providing a means for a fluid (e.g., the purified sample collected in cross flow filtration region 1708, which also contain some waste components from the blood sample and lysis buffer) to enter into channel 2208. At the opposite end of channel 2208 (i.e., at the output end) there are two waste outlets (2204*a* and 2204*b*), each of which provides a means for additional waste to exit channel 2208, and a sample outlet 2206 that provides a means for the desired concentrated fluid to exit channel 2208. As further shown in FIG. 22, two filters (2210*a* and 2210*b*) are disposed in channel 2208 and together form a separation chamber 2212 in channel 2208. Separation chamber 2212 includes an fluid entry point 2214 that is positioned downstream from inlet 2202 and a fluid exit point 2216 that is adjacent the output end of channel 2208 and that is in fluid communication with outlet 2206, but not in fluid communication with any of the waste outlets 2204.

Referring back to FIG. 17, it can be seen that after the intact nuclei exit filtration region 1708, the intact nuclei, as well as any waste matter not removed by filtration region 1708, will flow into the channel 2208 of concentrator 1712. Referring back now to FIG. 22, when the intact nuclei and any waste material enter channel 2208, the mixture will be forced to flow into separation chamber 2212 by, for example, a pressure differential (or other force) between the input end and the output end of channel 2208. When the mixture is in chamber 2212, some of the mixture will flow through filter 2210*a* towards waste outlet 2204*a*, some will flow through filter 2210*b* towards waste outlet 2204*b*, and the rest will flow the entire length of chamber 2212 and into channel 2223 and eventually to outlet 2206. For example, the pressure in chamber 2212 may be higher than the pressure at outlets 2204*a*, 2204*b* and 2206, thereby forcing some of the mixture to flow to the outlets. Advantageously, the filters 2210 are configured such that the intact nuclei in the mixture are not able to pass through or enter the filter, but any waste material is able to flow through the filter. Accordingly, the mixture that leaves chamber 2212 will have a higher concentration of intact nuclei than the mixture that entered chamber 2212.

As illustrated in FIG. 17, outlet 2206 of concentrator 1712 is in fluid communication with an inlet of an interface channel of interface region 1714. Accordingly, in some embodiments, as described above, a mixture containing a concentrated amount of intact nuclei may flow into the interface channels of interface region 1714 for further testing and analysis.

Figure 23:
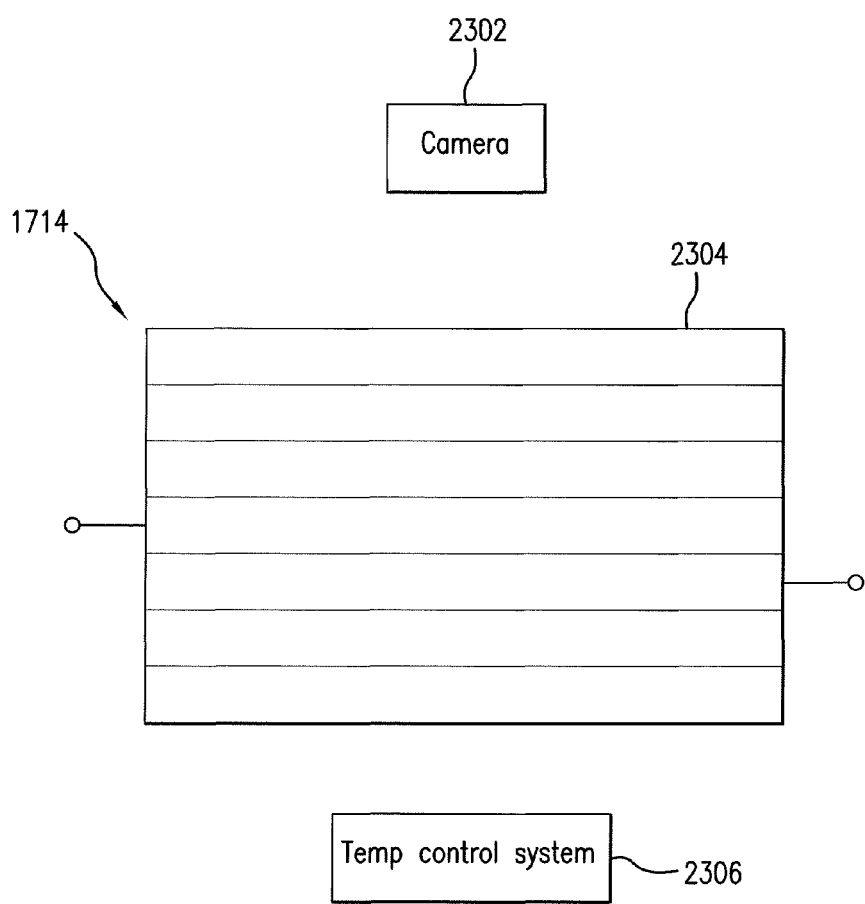
FIG. 23 illustrates a system for sample preparation in accordance with other embodiments of the present invention.

The interface region 1714 in accordance with one embodiment is further illustrated in FIG. 23. As shown in FIG. 23, interface region 1714 may contain a number of microfluidic channels 2304, such as, for example, 8 microfluidic channels. In some embodiments, the intact nuclei that exit concentrator 1712 are forced to flow through channels 2304 as is know in the art. As is also known in the art, as the intact nuclei flow, DNA from the intact nuclei may be released by lysing the nuclei. The DNA released from the intact nuclei may be amplified as they traverse channels 2304 using, for example, a PCR technique. In such an embodiment, a temperature control system 2306 controls the temperature of the DNA flowing though channels 2304 to create the PCR reaction. Thus, a portion of channels 2304 may be considered an amplification region. A camera 2302 may be positioned relative to channels 2304 to record fluorescent emissions from channels 2304 and thereby detect amplification of the DNA. Systems and methods for amplifying DNA and detecting the amplification of the DNA are described in the above-referenced patents.

In some embodiments, a concentrator is not used and the purified intact nuclei from the cross flow filtration region 1708 are caused to flow directly into the interface region 1714.

Figure 24:
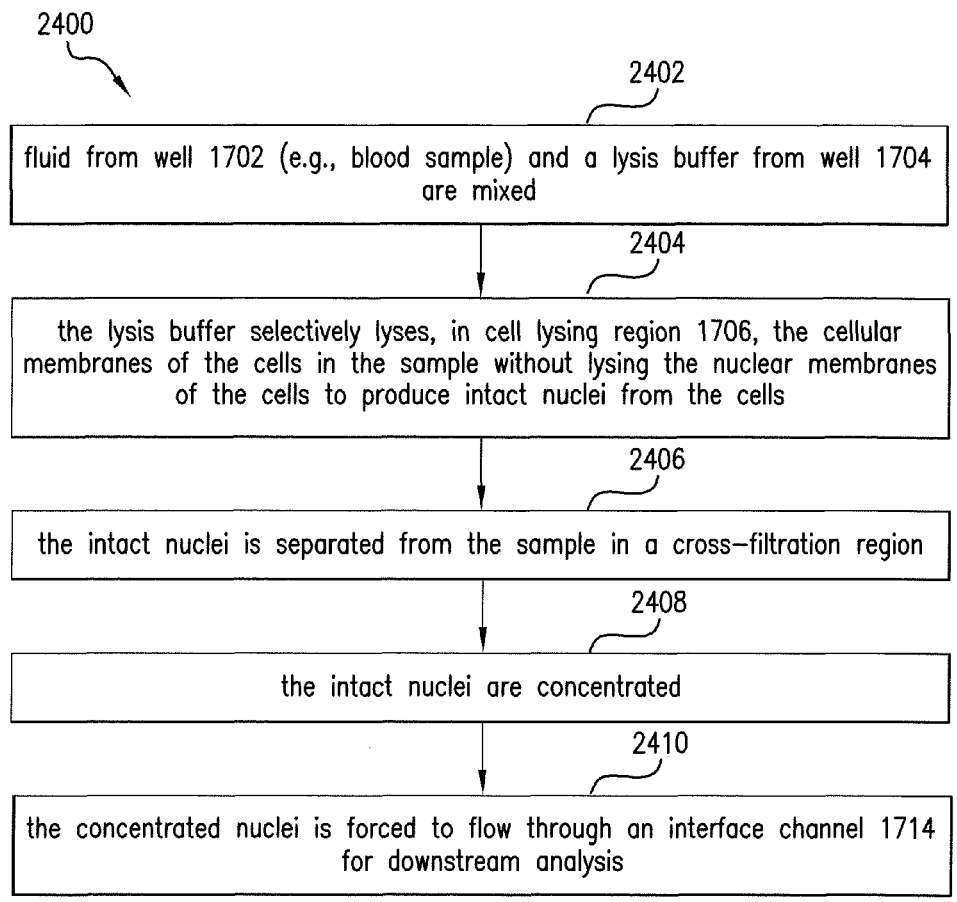
FIG. 24 is a flow chart illustrating a process for sample preparation according to an embodiment of the invention.

Referring now to FIG. 24, a flow chart is provided which illustrates a process 2400 according to an embodiment of the invention for using the system shown in FIG. 17. Process 2400 may begin in step 2402, wherein fluid from well 1702

(e.g., a blood sample) and a lysis buffer from well 1704 are mixed. That is, the blood sample and lysis buff are forced to flow out of wells 1702 and 1704, respectively, and into channel 1706, where the sample and lysis buffer mix. In some embodiments the fluids may be forced out of wells 1702 and 1704 by creating a pressure differential or an electrophoretic voltage.

In step 2404, while the mixture is flowing along channel 1706, the lysis buffer selectively lyses, in cell lysing region 1706, the cellular membranes of the cells in the sample without lysing the nuclear membranes of the cells to produce intact nuclei from the cells.

In step 2406, the intact nuclei is separated from the sample in a cross-flow filtration region 1708, which includes one or more cross-flow filters 1710 that has a pore size such that the intact nuclei are not permitted do not pass through the filter and the other components of the patient sample pass through the filter and are carried away by a cross-flow buffer that is controlled to flow through the cross-flow filtration region. In some embodiments, the cross-flow buffer is driven through the cross-flow filtration region by a pressure differential or by an electrophoretic voltage. In step 2408, which is optional, the intact nuclei are concentrated by concentrator 1712. In step 2410, the concentrated nuclei are forced to flow through an interface channel 1714 for downstream analysis.

In some embodiments, the cross-flow region may have multiple filters to filter out not only intact nuclei from the sample, but also bacteria and viruses. For example, the cross-flow filtration region may have three filters, one for separating nuclei from the sample, one for separation bacteria from the sample, and one for separating viruses from the sample, as described above in connection with FIG. 19. In other embodiments, the cross-flow filter 1710 is configured such that the purified sample from output end 1834 is recirculated back into the input end 1832 for additional passes through separation chamber 1814 for further purification. In one embodiment, this recirculation is accomplished by providing a channel connecting output end 1834 with input end 1832 to permit fluid flow there between, and controllably driving fluid from the output end into the input end by, for example, pressure differential.

Figure 25:
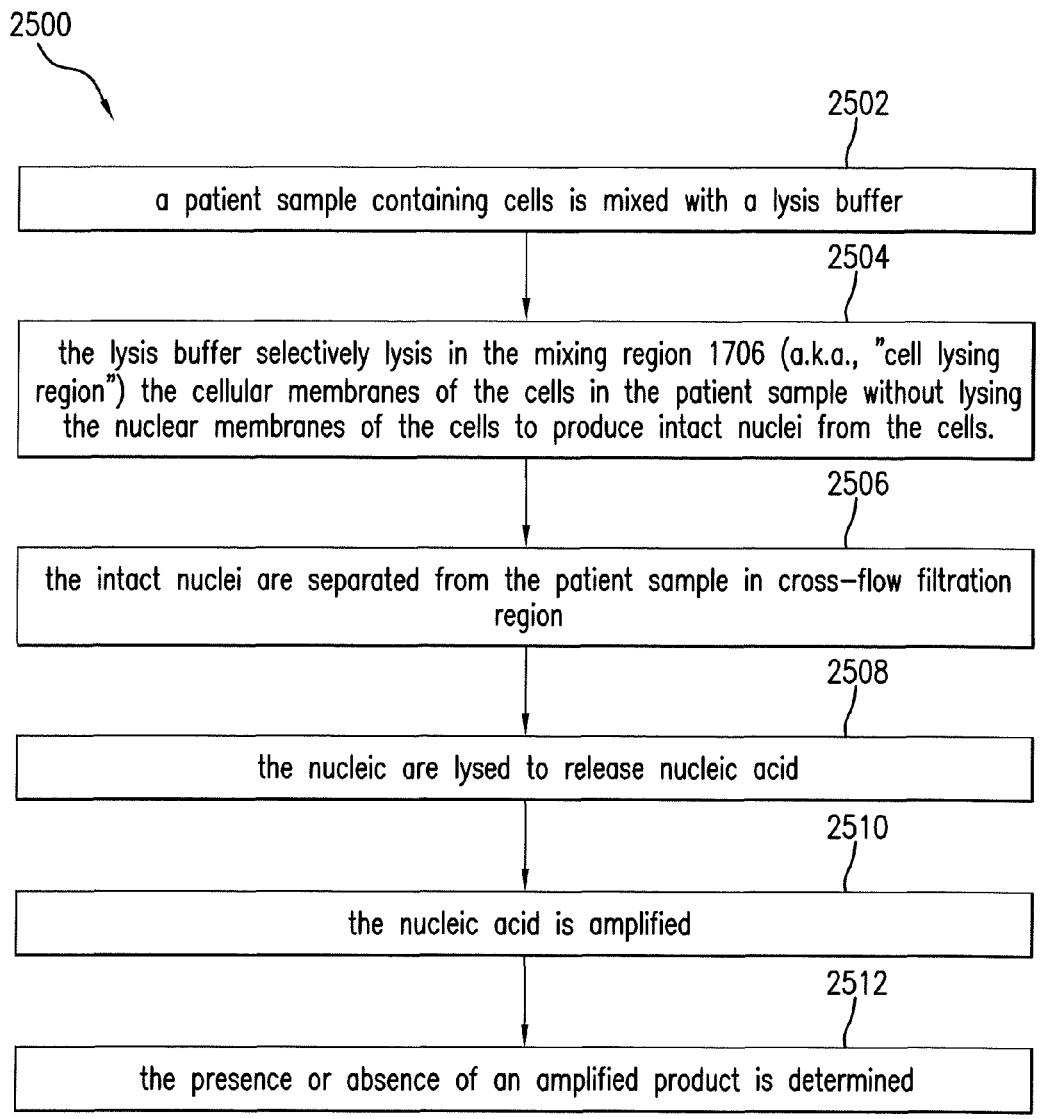
FIG. 25 is a flow chart illustrating a process for determining the presence or absence of a nucleic acid in a sample according to an embodiment of the invention.

Referring now to FIG. 25, a flow chart is provided illustrating a process 2500 of determining the presence or absence of a nucleic acid in a patient sample according to an embodiment of the invention. Process 2500 may begin in step 2502, where a patient sample containing cells is mixed with a lysis buffer in a mixing region of a microfluidic device (e.g., region 1706), wherein the lysis buffer selectively lyses cellular membranes without lysing nuclear membranes. Next, in step 2504, the lysis buffer selectively lysis in the mixing region 1706 (a.k.a., "cell lysing region") the cellular membranes of the cells in the patient sample without lysing the nuclear membranes of the cells to produce intact nuclei from the cells. In step 2506, the intact nuclei are separated from the patient sample in cross-flow filtration region 1708 as described above. In step 2508, the nuclei are lysed to release nucleic acid. In step 2510, the nucleic acid is amplified (e.g., amplified using PCR). In step 2512, the presence or absence of an amplified product is determined, wherein the presence of the amplified product indicates the presence of the nucleic acid in the patient sample. In some embodiments, the patient sample is first enriched for white blood cells prior to the selective lysis of the cellular membranes. In some embodiments, steps 2502-2508 are performed one microfluidic device and steps 2510-2512 are performed in a different microfluidic device.

In other embodiments, steps 2502-2506 are performed one microfluidic device and steps 2508-2512 are performed in a different microfluidic device.

Figure 26:
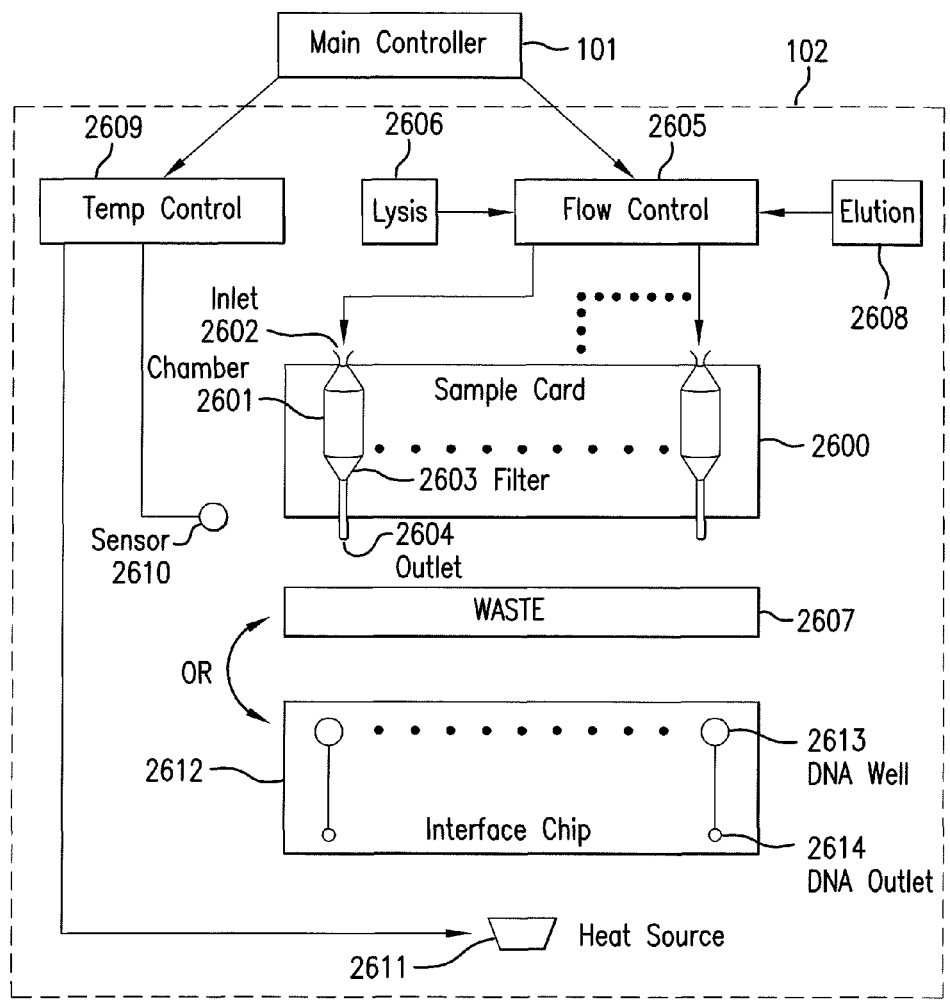
FIG. 26 shows a schematic illustration of a microfluidic device for sample preparation in accordance with other embodiments of the present invention.
Figure 27:
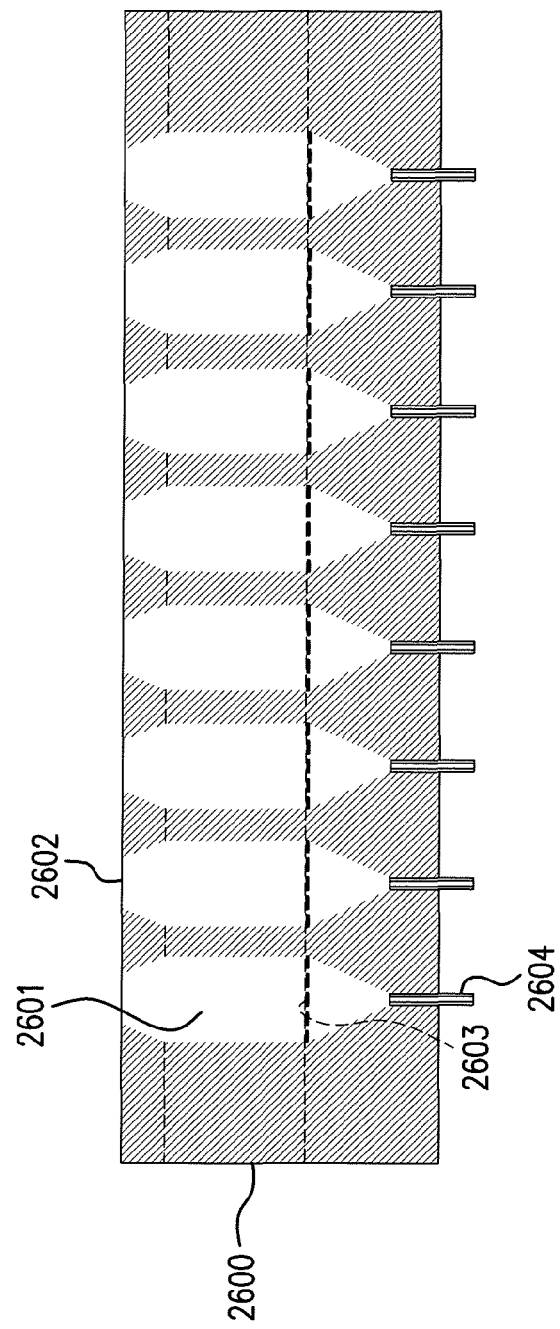
FIG. 27 illustrates a sample card in accordance with an embodiment of the invention.

Referring now to FIG. 26, subsystem 102 is illustrated in according with another embodiment. As shown in FIG. 26, the sample preparation subsystem 102 includes a sample card 2600 that has one or more chambers 2601 that are configured to hold one or more patient samples. Each of the one or more chambers 2601 comprises an inlet 2602, a filter 2603, and an outlet 2604. The sample card 2600 is removably insertable into the sample preparation subsystem 102, which allows the sample card 2600 to be loaded with the one or more patient samples, and then inserted into the sample preparation subsystem 102. Each inlet 2602 further comprises one or more channels which may or may not be in fluid communication with each other. FIG. 27 further illustrates one embodiment of the sample card 2600 containing one or more chambers 2601. As shown in FIG. 27, each chamber 2601 comprises an inlet 2602, a filter 2603, and an outlet 2604. The filter pore size may be between 1 to 15 um, and preferably is approximately 5 um.

As shown in FIG. 26, the sample preparation subsystem 102 includes a flow control system 2605 that controls the flow of a lysis buffer from a lysis buffer storage device 2606 into each chamber 2601 of the sample card 2600 through inlets 2602. The lysis buffer contained in the lysis buffer storage device 2606 selectively lyses cellular membranes to release nuclei and cell debris. The flow control system 2605 then causes the cell debris and lysis buffer to flow through the filter 2603, through outlets 2604, and into a removably insertable waste receptacle 2607, while leaving the nuclei trapped on the filter 2603. The waste receptacle 2607 is positionable beneath the outlets 2604 to receive the cell debris and lysis buffer from the chambers 2601. The lysis buffer does not lyse the nuclei from the patient sample. The flow control system 2605 also controls the flow of an elution buffer from an elution buffer storage device 2608 into each chamber 2601 of the sample card 2600 through the inlet 2602.

As shown in FIG. 26, the sample preparation subsystem 102 includes a temperature control system 2609 that controls the temperature of the sample card 2600. The temperature control system 2609 heats the sample card 2600, which causes the nuclei trapped on the filter 2603 to lyse, thereby releasing the DNA of the nuclei. In this embodiment, the temperature control system uses a sensor 2610 and a heat source 2611 to controllably and effectively heat the sample card to lyse the intact nuclei.

FIG. 26 further illustrates an interface chip 2612 which is removably insertable into the sample preparation subsystem 102. The interface chip 2612 is positionable beneath the sample card 2600 and is configured to receive the DNA released from the lysed nuclei trapped on the filter 2603. As shown in FIG. 26, the interface chip 2612 comprises one or more DNA sample wells 2613 which are in fluid communication with one or more DNA sample outlets 2614. When inserted into the subsystem 102, the DNA sample wells 2613 are each aligned with an outlet 2604 from the sample card 2600, which enables each DNA sample well 2613 to collect the DNA released by the lysed nuclei as the DNA exit the sample card 2600 through the outlet 2604.

In this embodiment, the main controller 101 communicates with the temperature control system 2609 and the flow control system 2605. As those skilled in the art will recognize, many options exist for a main controller 101, such as, for example, a general purpose computer or a special purpose computer. Other specialized control equipment known in the art could also serve the purpose of the main controller 101.

Figure 28:
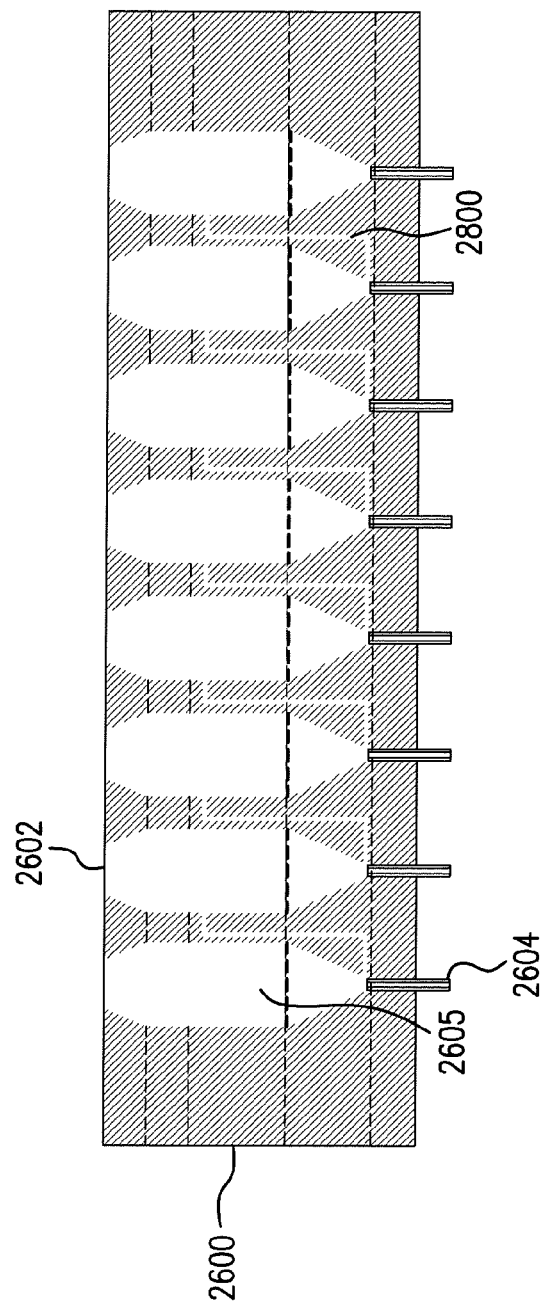
FIG. 28 illustrates a sample card in accordance with another embodiment of the invention.

Referring to FIG. 28, a sample card 2600 is illustrated with multiple chambers 2601 connected by fluidic channels 2800. In this embodiment, connecting chambers 2601 using a fluidic channel 2800 allows different numbers of samples to be tested in varying volumes. For example, in the embodiment shown where all chambers 2601 are in fluidic communication via fluidic channels 2800, the sample card 2600 would allow one patient sample to be tested in a larger volume because every chamber 2601, being in fluidic communication, would contain the same sample. Alternatively, if none of the chambers 2601 were in fluidic communication, as shown in FIG. 27, the sample card 2600 would allow testing of multiple patient samples simultaneously, in which each sample could be from the same patient or different patients. When none of the chambers 2601 are in fluidic communication, the number of patient samples to be tested would be limited by the number of chambers 2601 on the sample card 2600.

While FIG. 28 shows all chambers 2601 being connected, other arrangements are contemplated. The number of chambers 2601 connected together on a sample card 2600 could be many different combinations, which would allow for testing of a desired number of patient samples and a desired volume of each patient sample. For example, a sample card A200 could be configured to connect the chambers 2601 in pairs via fluidic channels 2800, which would reduce the number of different patient samples by half, while doubling the volume of each patient sample to be tested. The sample card 2600 can be made from various materials which might depend on the testing requirements of each application; the sample card 2600 can be reusable or disposable to reflect the requirements of each testing application.

Figure 29:
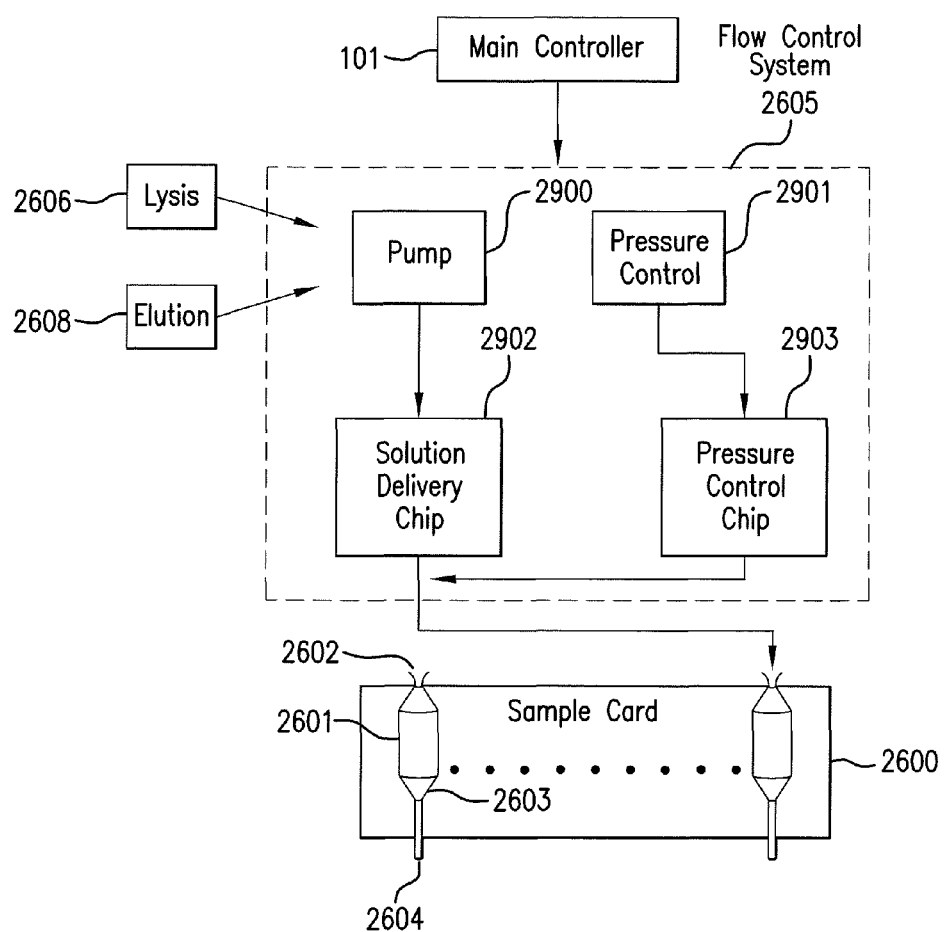
FIG. 29 illustrates a flow control system in accordance with an embodiment of the invention.

FIG. 29 further illustrates the flow control system 2605 according to one embodiment. As shown in FIG. 29, the flow control system 2605 is controlled by the main controller 101 and comprises a pump 2900, a pressure control system 2901, a solution delivery chip 2902, and a pressure control chip 2903. The pressure control system 2901 comprises an air source and a pressure sensor which allows the flow control system 2605 to control the delivery of the elution buffer and the lysis buffer to the sample card 2600 using pressure to move the solutions. The solution delivery chip 2902 comprises multiple channels for delivering lysis buffer and elution buffer to each chamber 2601 of the sample card 2600. The pressure control chip 2903 comprises multiple channels for providing pressure to each chamber 2601 of the sample card 2600. While this embodiment illustrates the use of a solution delivery chip 2902, a pump 2900, and a pressure control system 2901 in the flow control system 2605, the different components can be used in different combinations. For example, the pump 2900 and the solution delivery chip 2902 can be used without the pressure control system 2901. In another embodiment, the pressure control system 2901 can comprise multiple channels for controlling air pressure in each chamber 2601 of the sample card 2600.

Figure 30:
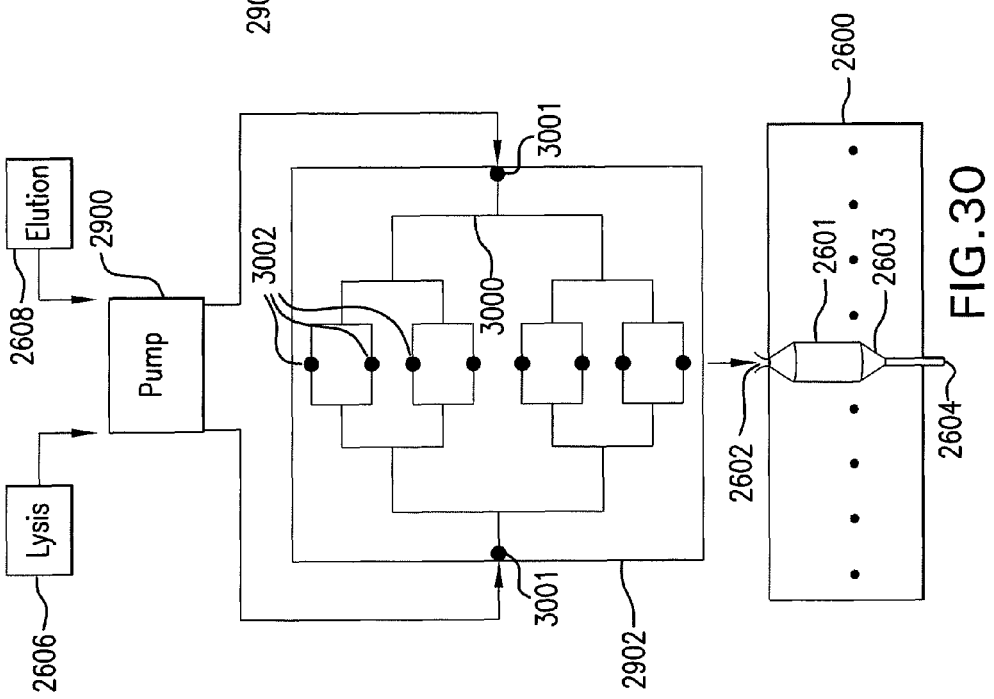
FIG. 30 illustrates a solution delivery chip in accordance with an embodiment of the invention.

Referring to FIG. 30, the solution delivery chip 2902 is illustrated according to one embodiment. As shown in FIG. 30, the solution delivery chip comprises multiple channels 3000 in fluidic communication the chambers 2601 of the sample card. The channels 3000 comprise one or more solution inlets 3001 which receive the buffers from the pump 2900. The channels 3000 further comprise one or more solution outlets 3002 that are in fluid communication with the inlets 2602 of the sample card 2600 which allows the lysis buffer and the elution buffer to be delivered to the chambers 2601 of the sample card 2600 via the solution outlets 3002 of the solution delivery chip 2902.

Figure 31:
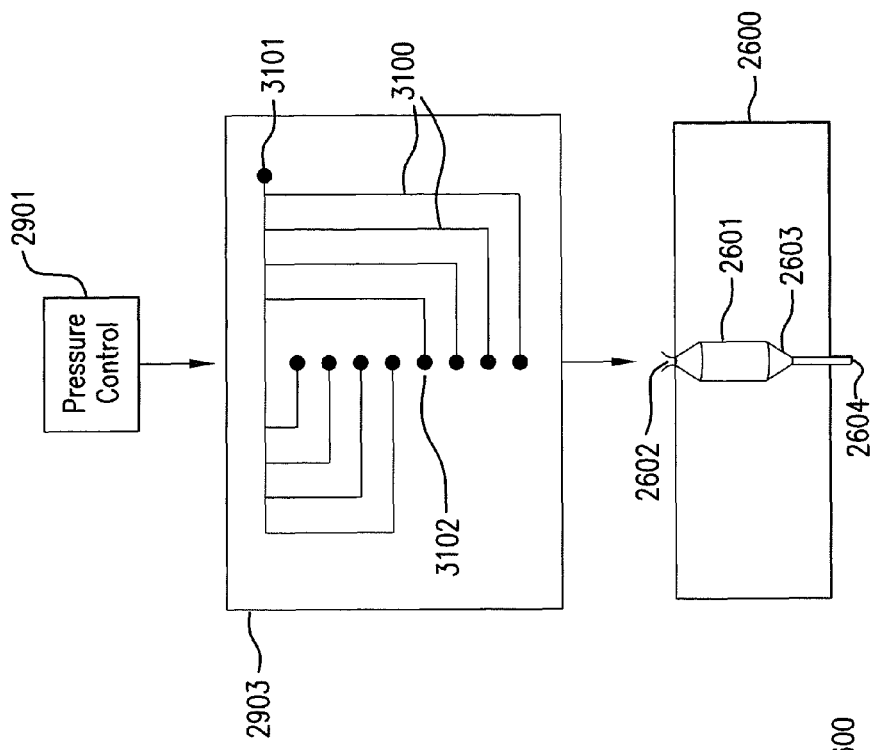
FIG. 31 illustrates a pressure control chip in accordance with an embodiment of the invention.

Referring to FIG. 31, the pressure control chip 2903 is illustrated according to one embodiment. As shown in FIG. 31, the pressure control chip 2903 comprises multiple pressure channels 3100, and each pressure channel 3100 is in fluid communication with a pressure inlet 3101 and a pressure outlet 3102. In this embodiment, each pressure channel is in fluid communication with the same pressure inlet 3101; however, other embodiments are contemplated where there may be more than one pressure inlet 3101. The pressure inlet 3101 is in fluid communication with the pressure control system 2901 in order to deliver pressure to the pressure control chip 2903. The pressure outlets 3102 are in fluid communication with the inlets 2602 of the sample card 2600, which allows the pressure control chip 293 to deliver pressure to the chambers 2601 of the sample card 2600.

Figure 32:
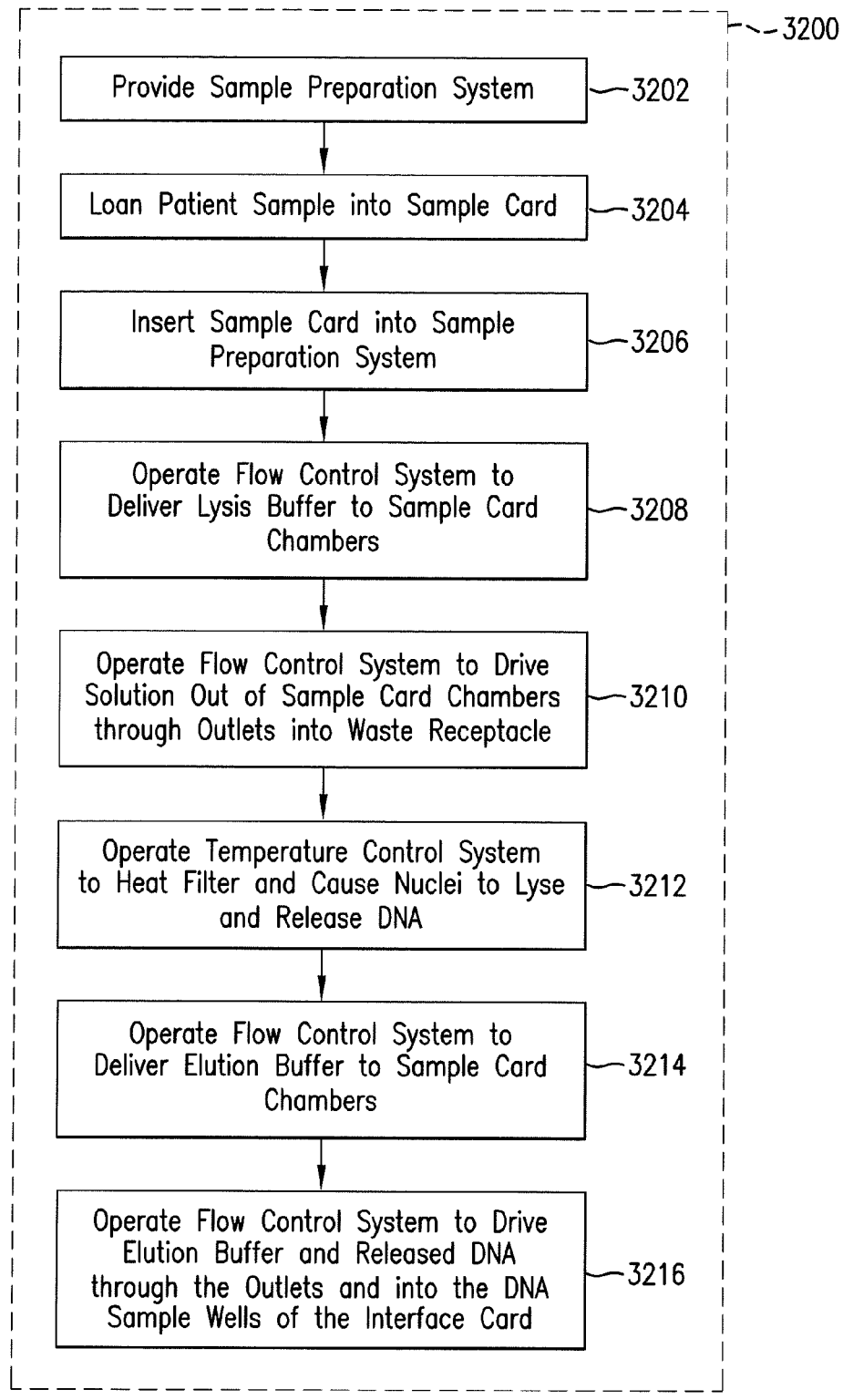
FIG. 32 is a flow chart illustrating a process for sample preparation according to an embodiment of the invention.

FIG. 32 is a flowchart illustrating a method 3200 for isolating DNA cells in a patient sample. While the method 3200 is not limited to the system provided in FIG. 26, one preferred embodiment of the method can utilize a system similar to that shown in FIG. 26, and FIG. 26 is used for reference purposes to assist in describing the method. As shown in FIG. 32, in step 3202 a sample preparation system 102 is provided, wherein the system comprises: (i) a sample card 2600 having multiple chambers 2601, wherein each chamber 2601 comprises an inlet 2602, a filter 2603, and an outlet 2604, where the sample card 2600 is removably insertable into the sample preparation subsystem 102; (ii) a flow control system 2605 for controlling flow of a lysis buffer and an elution buffer to each chamber 2601 of the sample card 2600; (iii) a temperature control system 2609 for heating the filter 2603 in the sample card 2600; (iv) a removably insertable waste receptacle 2607 which is positionable beneath the sample card 2600; and (v) an interface chip 2612 comprising multiple DNA sample wells 2613 and DNA sample outlets 2614, where the interface chip 2612 is positionable beneath the sample card 2600.

In step 3204, the patient sample is loaded into the chambers 2601 of the sample card 2600. In step 3206, the sample card 2600 containing the patient sample is inserted into the sample preparation system 102. In step 3208, the flow control system 2605 delivers a lysis buffer from the lysis buffer storage device 2606 to the chamber 2601 of the sample card 2600 through the inlet 2602. The lysis buffer selectively lyses the cellular membranes of the patient sample without lysing the nuclear membranes of the nuclei. The reaction produces a solution comprising a lysis buffer, intact nuclei and cellular debris, in the chamber 2601 of the sample card 2600. In step 3210, the removably insertable waste receptacle 2607 is positioned below the sample card 2600 and the flow control system 2605 operates to drive the solution through the filter 2603 of the chamber 2601. The filter 2603 traps the intact nuclei from the solution while the lysis buffer and the cellular debris are driven out of the chamber 2601 through the outlet 2604 by the flow control system 2605. The lysis buffer and cellular debris are collected when exiting the chamber 2601 through the outlet 2604 in the waste receptacle 2607.

In step 3212, the temperature control system 2609 operates to heat the filter 2603, which heats the intact nuclei trapped in the filter 2603. The heating of the intact nuclei causes the nuclei to lyse, which releases DNA from the nuclei. In step 3214, the flow control system 2605 operates to deliver the elution buffer from the elution buffer storage device 2608 to the chamber 2601 of the sample card 2600 through the inlet 2602. In step 3216, the interface card 2612 is positioned beneath the sample card 2600, and the flow control system 2605 operates to drive the elution buffer and the DNA through the outlet 2604 of the chamber 2601 while leaving the lysed nuclei on the filter 2603. The elution buffer and DNA are deposited in the DNA sample well 2613 of the interface chip 2612 after exiting the chamber 2601 though the outlet 2604. This method thus allows the DNA to be isolated from the patient sample.

An optional step following the DNA isolation described above can be to deliver the lysis buffer from the lysis buffer containment device 2606 into the chambers 2601 of the sample card 2600 using the flow control device 2605, then drive the solution out of the chamber 2601 through the outlet 2604 by operation of the flow control system 2605 in order to clean the filter 2603. This optional step can be repeated multiple times to provide the desired level of cleanliness of the filter 2603.

While various embodiments of the present invention have been described above, it should be understood that they have been presented by way of example only, and not limitation. Thus, the breadth and scope of the present invention should not be limited by any of the above-described exemplary embodiments. Variations of the embodiments described above may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A microfluidic device for purifying DNA from a sample comprising:
    (a) a sample port and lysis buffer port in fluid communication with a mixing region of the micro fluidic device, said mixing region being configured to permit mixing of a sample from the sample port and lysis buffer from the lysis buffer port mix;
    (b) a cell lysis region in fluid communication with the mixing region, said cell lysis region being configured to permit the lysis buffer to selectively lyse cellular membranes of cells in the sample without lysing nuclear membranes of the cells to produce intact nuclei from the cells in the sample;
    (c) a nuclei trapping region wherein intact nuclei from the sample are trapped by a filter via cross flow filtration while other components of the sample flow through the filter and into a waste collection region of the microfluidic device, said nuclei trapping region being in fluid communication with said cell lysis region;
    (d) a nuclei lysis region in which the nuclear membranes of the intact nuclei are lysed to release the DNA;
    (e) an elution buffer port in fluid communication with the nuclei trapping region and the nuclei lysing region, wherein elution buffer from the elution buffer port can be controlled to flow through the nuclei trapping region and the nuclei lysing region thereby lysing the nuclear membranes of the trapped intact nuclei to release the DNA; and
    (f) a DNA collection region in said microfluidic device wherein DNA released from the trapped intact nuclei is collected.

2. The microfluidic device of claim 1, wherein the elution buffer comprises Tris buffer, KCl and a zwitterion.

3. The microfluidic device of claim 1, further comprising a heat source which is configured to provide heat to the intact nuclei in the nuclei lysis region sufficient to lyse the nuclear membranes thereby releasing the DNA.

4. The microfluidic device of claim 3, wherein the heat source is controlled to heat the nuclei for approximately 1 to 10 minutes at a temperature in the range of approximately 35° C. to 95° C.

5. The micro fluidic device of claim 4, wherein the heat source is controlled to heat the nuclei for approximately 7 minutes at a temperature of approximately 50° C.

6. The microfluidic device of claim 3, wherein the DNA released from the lysed nuclei flows to the DNA collection region of the microfluidic device by flowing an elution buffer over the DNA.

7. The microfluidic device of claim 1, wherein the filter is made of silicon, glass, polymers, polyester, polycarbonate or nitrocellulose.

8. The microfluidic device of claim 1, wherein the filter has a round or rectangular shape.

9. The microfluidic device of claim 1, wherein the filter has a pore size from approximately 500 nm to 10 μm.

10. The microfluidic device of claim 9, wherein the filter has a pore size from approximately 0.5 μm to 10 μm.

11. The microfluidic device of claim 1, wherein the microfluidic device comprises multiple layers.

12. The microfluidic device of claim 11, wherein the microfluidic device further comprises:
    (1) a first layer comprising the lysis buffer port, the sample port, an elution buffer port, a purified DNA collection port and a waste port;
    (2) a second layer comprising a network of micro channels that transports the lysis buffer solution and the sample to the mixing region of the microfluidic device;
    (3) a third layer comprising a network of micro channels;
    (4) the filter located between the second and third layers, wherein the sample and the lysis buffer solution mix in the mixing region and flow in the micro channels to the cell lysis region, and wherein the sample and the lysis buffer solution flow from the cell lysis region to the filter in the nuclei trapping region, and wherein the other components of the sample flow through the filter and into a microchannel in the third layer and to the waste collection region of the micro fluidic device, and wherein the DNA released from the nuclei flows through the filter and into a microchannel located in the third layer and to the DNA collection region.

13. The micro fluidic device of claim 11, wherein the microfluidic device further comprises:
    (1) a first layer comprising the lysis buffer port, the sample port, an elution buffer port, a purified DNA collection port and a waste port;
    (2) a second layer comprising a network of micro channels that transports the lysis buffer solution and the sample to the mixing region of the microfluidic device;
    (3) a third layer comprising a hole through which fluid flows from the micro channels in the second layer and onto the filter;
    (4) a fourth layer comprising a hole through which fluid flows from the filter and into microchannels located in a fifth layer, said fifth layer further comprising the waste collection region and the DNA collection region.

14. A microfluidic device for purifying DNA from a sample comprising:
- (a) a cell lysis region configured such that a lysis buffer is permitted to mix with the sample resulting in the selective lysing of cellular membranes of cells in the sample without lysing nuclear membranes of the cells to produce intact nuclei from the cells in the sample;
- (b) a cross-flow filtration region in which intact nuclei are separated from other components of the sample by a filter, said filter having a pore size such that the intact nuclei do not pass through the filter and the other components of the sample pass through the filter and are carried away by a cross-flow buffer that is controlled to flow through the cross-flow filtration region;
- (c) an interface channel in fluid communication with said cross-flow filtration region through which purified nuclei flow for downstream analysis.

15. The microfluidic device of claim 14, wherein the cross-flow filtration region comprises:
- (i) a microfluidic separation channel in fluid communication with the cell lysis region and configured to receive the intact nuclei and the other components of the sample from the cell lysis region, and wherein the filter is constructed in the microfluidic channel; and
- (ii) a cross-flow buffer port configured to permit the cross-flow buffer to flow across the micro fluidic separation channel and through the filter;

wherein the cross-flow buffer, as it flows across the separation channel, facilitates removal of said other contents of the sample from the separation channel through the filter, and wherein the intact nuclei flow through the separation channel.

16. The microfluidic device of claim 14, wherein the flow of one of the lysed sample and the cross-flow buffer is driven by a pressure differential and the flow of the other of the lysed sample and cross-flow buffer is driven by pressure differential or an electrophoretic voltage potential.

17. The microfluidic device claim 14, wherein the pore size of the filter is between approximately 2 µm to 10 µm.

18. The microfluidic device claim 17, wherein the pore size of the filter is approximately 5 µm.

19. The microfluidic device claim 14, wherein the filter is a membrane.

20. The microfluidic device of claim 14, wherein the filter is an array of pillars.

21. The microfluidic device claim 14, wherein the cross-flow filtration region is configured to separate the intact nuclei, bacteria and viruses from the lysed sample.

22. The microfluidic device of claim 21, wherein the cross-flow filtration region comprises a first filter to separate the intact nuclei, a second filter to separate bacteria and a third filter to separate viruses.

23. The microfluidic device of claim 22, wherein the first filter is located closest to a cross-flow buffer port, the second filter located next closest to the cross-flow buffer port, and the third filter located furthest from the cross-flow buffer port.

24. The microfluidic device claim 22, wherein the pore size of the first filter is between approximately 2 µm to 10 µm, the pore size of the second filter is between approximately 0.2 µm to 2 µm, and the pore size of the third filter is between approximately 10 nm to 400 nm.

25. The microfluidic device claim 24, wherein the pore size of the first filter is approximately 8 µm, the pore size of the second filter is approximately 0.4 µm, and the pore size of the third filter is approximately 100 nm.

26. The microfluidic device of claim 14, further comprising more than one cross-flow filtration region, each receiving a portion of the lysed sample from the cell lysis region, and each in fluid communication with one or more interface channels.

27. The microfluidic device of claim 26, wherein the filter of one cross-flow filtration region has a pore size that is different from the pore size of one other cross-flow filtration region.

28. The microfluidic device of claim 14, further comprising a nuclei concentration region in which the intact nuclei from the cross-flow filtration region are concentrated.

29. The micro fluidic device claim 28, wherein the nuclei concentration region comprises a concentration channel having a sample input section, a sample outlet section and a wall portion configured to prevent intact nuclei from flowing through said wall portion and to allow the other contents of the sample to flow through said wall portion.

30. The microfluidic device of claim 29, wherein said wall portion is a filter.

31. The microfluidic device of claim 30, wherein the filter comprises a set of pillars placed along the concentration channel.

32. The microfluidic device of claim 14, wherein the sample comprises white blood cells.

33. The microfluidic device of claim 14, wherein the downstream analysis comprises an amplification reaction in which nucleic acid is amplified and/or a detection procedure for determining the presence or absence of an amplified product.

34. A microfluidic system for purifying DNA from cells in a sample comprising:
- (a) a microfluidic device;
- (b) a cell lysis region in the microfluidic device configured such that a lysis buffer is permitted to mix with the sample resulting in the selective lysing of cellular membranes of cells in the sample without lysing nuclear membranes of the cells to produce intact nuclei from the cells in the sample;
- (c) a cross-flow filtration region in the micro fluidic device in which intact nuclei are separated from other components of the sample by a filter, said filter having a pore size such that the intact nuclei do not pass through the filter and the other components of the sample pass through the filter and are carried away by a cross-flow buffer that is controlled to flow through the cross-flow filtration region;
- (d) a nuclei lysis region in the micro fluidic device in which the nuclear membranes of the intact nuclei are lysed to release the DNA, said nuclei lysis region being in fluid communication with the cross-flow filtration region;
- (e) an amplification reaction region in the microfluidic device in which the nucleic acid is amplified; and
- (f) a detection region in the microfluidic device for determining the presence or absence of an amplified product.

35. The system of claim 34, wherein the nuclei lysis region is part of the amplification reaction region.

36. The system of claim 34, wherein regions (b)-(d) are in one micro fluidic device and regions (e) and (f) are in a second microfluidic device.

37. A microfluidic system for isolating DNA from cells in a sample comprising:
- (a) a lysis buffer storage device for storing a lysis buffer, wherein the lysis buffer selectively lyses cellular membranes without lysing nuclear membranes;
- (b) an elution buffer storage device for storing an elution buffer;
- (c) a sample card having multiple chambers for receiving the sample, wherein each chamber comprises an inlet, a filter and an outlet;

(d) a flow control system for controlling flow of the lysis buffer and the elution buffer to each chamber of the sample card, said flow control system controlling the flow of lysis buffer into each chamber of the sample card such that the lysis buffer selectively lyses cellular membranes to release nuclei and cell debris causing the cell debris to flow through the filter into a waste receptacle positionable beneath the sample card and without lysing nuclear membranes of nuclei in the sample which become trapped on the filter;

(e) a temperature control system for heating the filter in the sample card sufficient to lyse nuclei trapped on said filter and release DNA;

(f) an interface chip comprising multiple DNA sample wells and DNA sample outlets, wherein said interface chip is positionable beneath the sample card and is configured to receive the DNA released from the lysed nuclei trapped on said filter; and (g) a main controller in communication with (a) the temperature control system, and (b) the flow control system.

38. The microfluidic system of claim 37, wherein the temperature control system comprises a heating source and a heat sensor.

39. The microfluidic system of claim 37, wherein the flow control system comprises a pump and a solution delivery chip, wherein the solution delivery chip comprises multiple channels for delivering lysis buffer and elution buffer to each chamber of the sample card.

40. The micro fluidic system of claim 37, wherein the flow control system further comprises a pressure control system, said pressure control system comprises an air source, a pressure sensor for controlling the delivery of the elution buffer and the lysis buffer to each chamber of the sample card.

41. The microfluidic system of claim 37, wherein the multiple chambers of the sample card are in fluid communication with one another.

42. The microfluidic system of claim 37, wherein the sample card is disposable.

43. The micro fluidic system of claim 37, wherein the sample card is configured to contain multiple different samples.

44. The microfluidic system of claim 41, wherein the sample card is configured to contain one sample in multiple chambers.

45. A microfluidic system for determining the presence or absence of a nucleic acid in a sample comprising:
(a) a microfluidic device comprising a sample preparation region, an amplification reaction region and a detection region; said sample preparation region comprising:
(i) a lysis buffer storage device for storing a lysis buffer, wherein the lysis buffer selectively lyses cellular membranes without lysing nuclear membranes;
(ii) an elution buffer storage device for storing an elution buffer;
(iii) a sample card having multiple chambers for receiving the sample, wherein each chamber comprises an inlet, a filter and an outlet, said sample card being removably insertable into said sample preparation region of said microfluidic device;
(iv) a flow control system for controlling flow of the lysis buffer and the elution buffer to each chamber of said sample card, said flow control system controlling the flow of lysis buffer into each chamber of the sample card such that the lysis buffer selectively lyses cellular membranes to release nuclei and cell debris causing the cell debris to flow through the filter into a waste receptical positionable beneath the sample card and without lysing nuclear membranes of nuclei in the sample which become trapped on the filter;
(v) a temperature control system for heating the filter in the sample card sufficient to lyse nuclei trapped on said filter and release DNA;
(vi) an interface chip comprising multiple DNA sample wells and DNA sample outlets, wherein said interface chip is positionable beneath the sample card and is configured to receive the DNA released from the lysed nuclei trapped on said filter; and
(b) a main controller in communication with (a) the temperature control system, (b) the flow control system, and (c) the microfluidic chip,
wherein the main controller controls the flow of DNA from the interface chip to the amplification region and/or the detection region of the micro fluidic chip.

46. The microfluidic system of claim 45, wherein the temperature control system comprises a heating source and a heat sensor.

47. The micro fluidic system of claim 45, wherein the flow control system comprises a pump and a solution delivery chip, wherein the solution delivery chip comprises multiple channels for delivering lysis buffer and elution buffer to each chamber of the sample card.

48. The microfluidic system of claim 45, wherein the multiple chambers of the sample card are in fluid communication.

49. The microfluidic system of claim 45, wherein the flow control system further comprises a pressure control system, said pressure control system comprises an air source, a pressure sensor for controlling the delivery of the elution buffer and the lysis buffer to each chamber of the sample card.

50. The microfluidic system of claim 45, wherein the multiple chambers of the sample card are in fluid communication, wherein a sample in one chamber can be driven into other chambers.

51. The micro fluidic system of claim 45, wherein the sample card is disposable.

52. The microfluidic system of claim 51, wherein the pressure control system comprises an air source, a pressure sensor and multiple channels for controlling air pressure in each chamber of the sample card.

* * * * *